(12) United States Patent
Kleyer et al.

(10) Patent No.: US 9,493,634 B2
(45) Date of Patent: Nov. 15, 2016

(54) ADDITIVE FOR A SILICONE ENCAPSULANT

(71) Applicant: Dow Corning Corporation, Midland, MI (US)

(72) Inventors: Don L Kleyer, Hemlock, MI (US); Fumito Nishida, Midland, MI (US); Randall G Schmidt, Midland, MI (US); Adam C Tomasik, Mount Pleasant, MI (US)

(73) Assignee: DOW CORNING CORPORATION, Midland, MI (US)

( * ) Notice: Subject to any disclaimer, the term of this patent is extended or adjusted under 35 U.S.C. 154(b) by 0 days.

(21) Appl. No.: 14/906,575

(22) PCT Filed: Sep. 2, 2014

(86) PCT No.: PCT/US2014/053696
§ 371 (c)(1),
(2) Date: Jan. 21, 2016

(87) PCT Pub. No.: WO2015/034821
PCT Pub. Date: Mar. 12, 2015

(65) Prior Publication Data
US 2016/0168359 A1 Jun. 16, 2016

Related U.S. Application Data

(60) Provisional application No. 61/873,160, filed on Sep. 3, 2013.

(51) Int. Cl.
*C08K 5/5419* (2006.01)
*C07F 7/08* (2006.01)
*C09D 183/04* (2006.01)

(52) U.S. Cl.
CPC .......... *C08K 5/5419* (2013.01); *C07F 7/0859* (2013.01); *C07F 7/0872* (2013.01); *C09D 183/04* (2013.01)

(58) Field of Classification Search
None
See application file for complete search history.

(56) References Cited

U.S. PATENT DOCUMENTS

2012/0065308 A1   3/2012   Sumi et al.

FOREIGN PATENT DOCUMENTS

| EP | 0231519 A2 | 8/1987 |
| EP | 0699717 A2 | 3/1996 |
| WO | 2013/052838 A1 | 4/2013 |

OTHER PUBLICATIONS

Gradeff et al. "Synthesis of Yttrium and Lanthanide Silyloxy Complexes from Anhydrous Nitrate and Oxo Alkoxide Precursors and the X-ray Crystal Structure of [Ce(OSiPh3)3(THF)3](THF)" Inorg. Chem. 1990, 29, 420-424.*
Sroor et al. "Tetravalent Chemistry: Organometallic" Encyclopedia of Inorganic and Bioinorganic Chemistry, 2011-2012, 14 pages.*
PCT/US2014/053696 Search Report Dated Nov. 27, 2014.
Kleyer et al., U.S. Appl. No. 14/906,579, filed Jan. 21, 2016.
Yoshida et al., U.S. Appl. No. 14/769,131, filed Aug. 20, 2015.

* cited by examiner

Primary Examiner — Robert S Loewe
(74) Attorney, Agent, or Firm — Dow Corning Corporation

(57) ABSTRACT

An additive for a silicone encapsulant has the structure: (I) $R^1Ce(OSi-R^2)$ I I a $R^3$ wherein a is 3 or 4, wherein $R^1$ and $R^2$ are each $-O-Si(R^4)(R^5)(R^6)$ and each of $R^4$, $R^5$, and $R^6$ is independently chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups, and wherein $R^3$ is independently chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups. More specifically, the cerium is cerium (III) or (IV). The additive is formed using a method that includes the step of reacting cerium metal or a cerium (III) or (IV) compound with a hydroxyl functional organosiloxane. An encapsulant includes the additive and a polyorganosiloxane. The encapsulant can be utilized to form a device that includes an optoelectronic component and the encapsulant disposed on the optoelectronic component. The device is formed using a method that includes the step of disposing the encapsulant on the optoelectronic device.

18 Claims, 13 Drawing Sheets

ADDITIVE FOR A SILICONE ENCAPSULANT

CROSS REFERENCE TO RELATED APPLICATIONS

This application is a U.S. national stage filing under 35 U.S.C. §371 of PCT Application No. PCT/US14/53696 filed on 2 Sep. 2014, currently pending, which claims the benefit of U.S. Provisional Patent Application No. 61/873,160 filed 3 Sep. 2013 under 35 U.S.C. §119(e). PCT Application No. PCT/US14/53696 and U.S. Provisional Patent Application No. 61/873,160 are hereby incorporated by reference.

FIELD OF THE DISCLOSURE

The present disclosure generally relates to an additive for a silicone encapsulant. More specifically, the additive has a particular structure and includes cerium (III) or (IV), and includes a series of ligands that include silicon, bonded to the cerium.

DESCRIPTION OF THE RELATED ART

Silicone encapsulants can be used to encapsulate optoelectronic components such as light emitting diodes, photovoltaic cells, reflectors, die attaches, and the like. However, these encapsulants traditionally suffer from yellowing over time and embrittlement, i.e., loss of ductility causing breakage or fragmentation. As a result, additives have been added to silicone encapsulants in an attempt to mitigate these problems. Yet, most additives are strongly colored and are unusable in many optoelectronic applications. Other additives, although not colored, are very heavy and settle out of the encapsulants, rendering the encapsulants unusable for many applications. Still other additives, although not colored and not heavy, are ineffective in reducing yellowing and embrittlement. Accordingly, there remains an opportunity to develop an improved additive for use in a silicone encapsulant.

SUMMARY OF THE DISCLOSURE

The present disclosure provides an additive for a silicone encapsulant and a method of forming the additive. The additive has the structure:

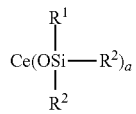

wherein subscript a is 3 or 4, wherein $R^1$ and $R^2$ are each —O—Si$(R^4)(R^5)(R^6)$ and each of $R^4$, $R^5$, and $R^6$ is independently chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups, and wherein $R^3$ is independently chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups. More specifically, the cerium is cerium (III) or (IV). The method includes the step of reacting cerium metal or a cerium (III) or (IV) compound with a hydroxyl functional organosiloxane, e.g. in at least a 3:1 molar ratio when a cerium (III) compound or cerium metal is utilized or at least a 4:1 molar ratio when a cerium (IV) compound or cerium metal is utilized.

This disclosure also provides an encapsulant that includes the additive and a polyorganosiloxane. The encapsulant can be utilized to form a device that includes an optoelectronic component and the encapsulant disposed on the optoelectronic component. The disclosure also provides a method of forming the device that includes the step of disposing the encapsulant on the optoelectronic device.

BRIEF DESCRIPTION OF THE DRAWINGS

Other advantages of the present disclosure will be readily appreciated, as the same becomes better understood by reference to the following detailed description when considered in connection with the accompanying drawings wherein.

DETAILED DESCRIPTION OF THE DISCLOSURE

Figure 1:
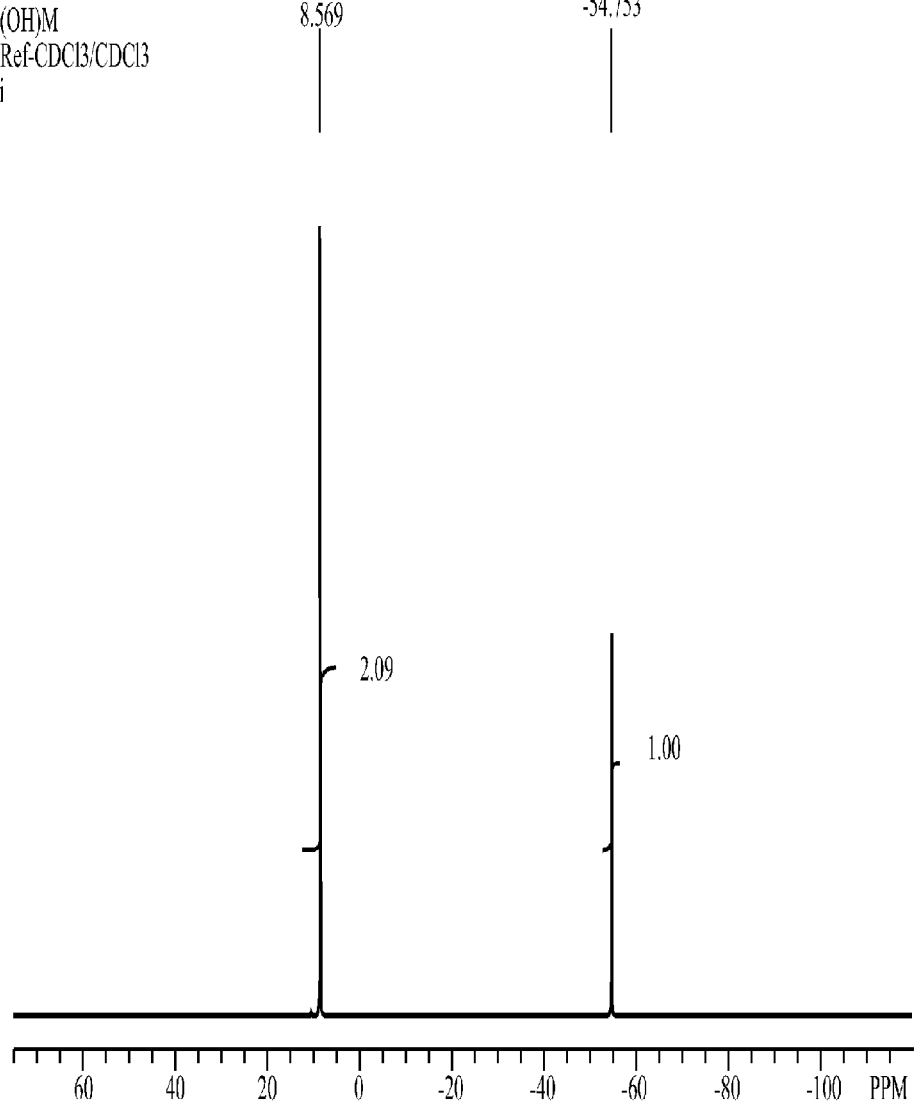
FIG. 1 is a $^{29}$Si NMR spectrograph of 1,1,1,3,5,5,5-heptamethyltrisiloxan-3-ol.
Figure 2:
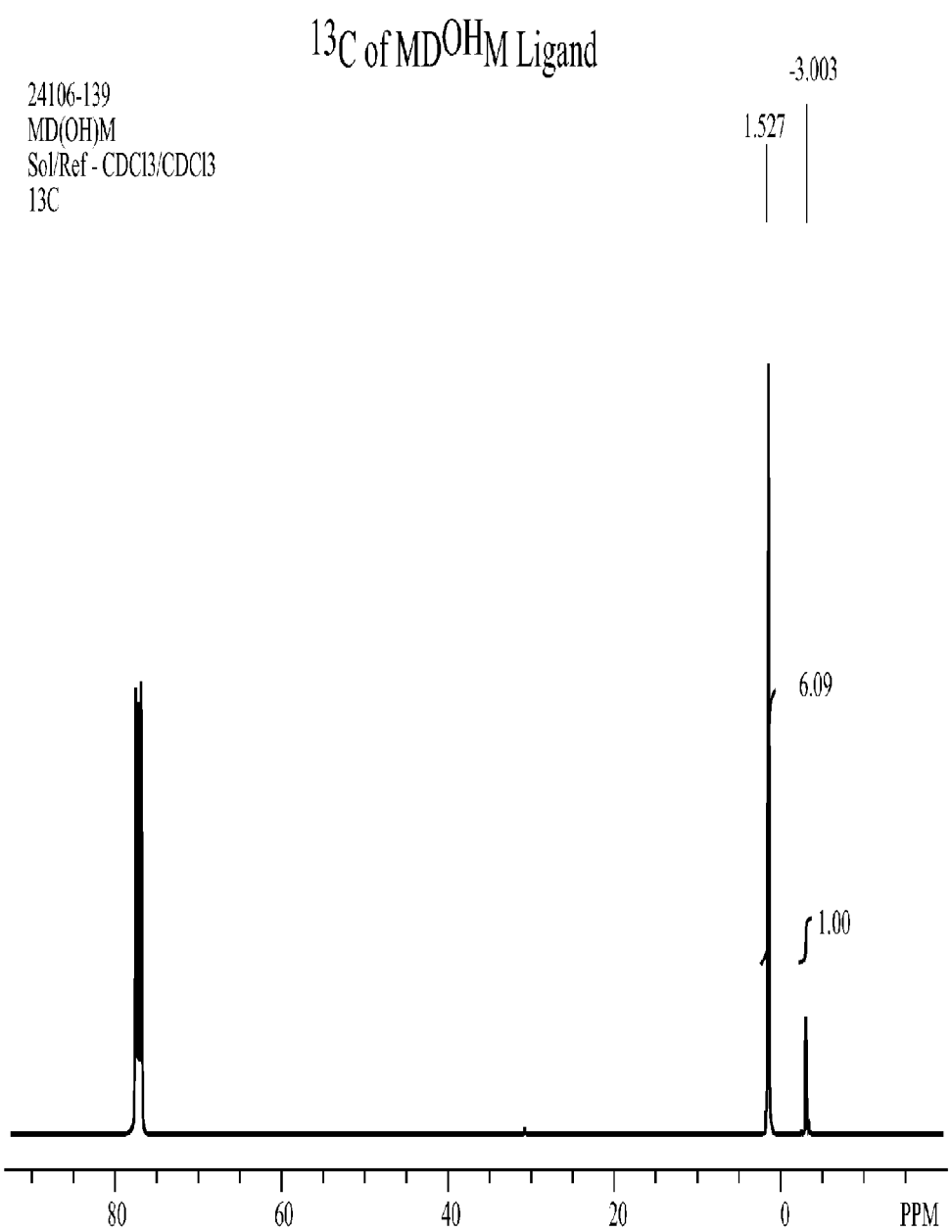
FIG. 2 is a $^{13}$C NMR spectrograph of 1,1,1,3,5,5,5-heptamethyltrisiloxan-3-ol.
Figure 3:
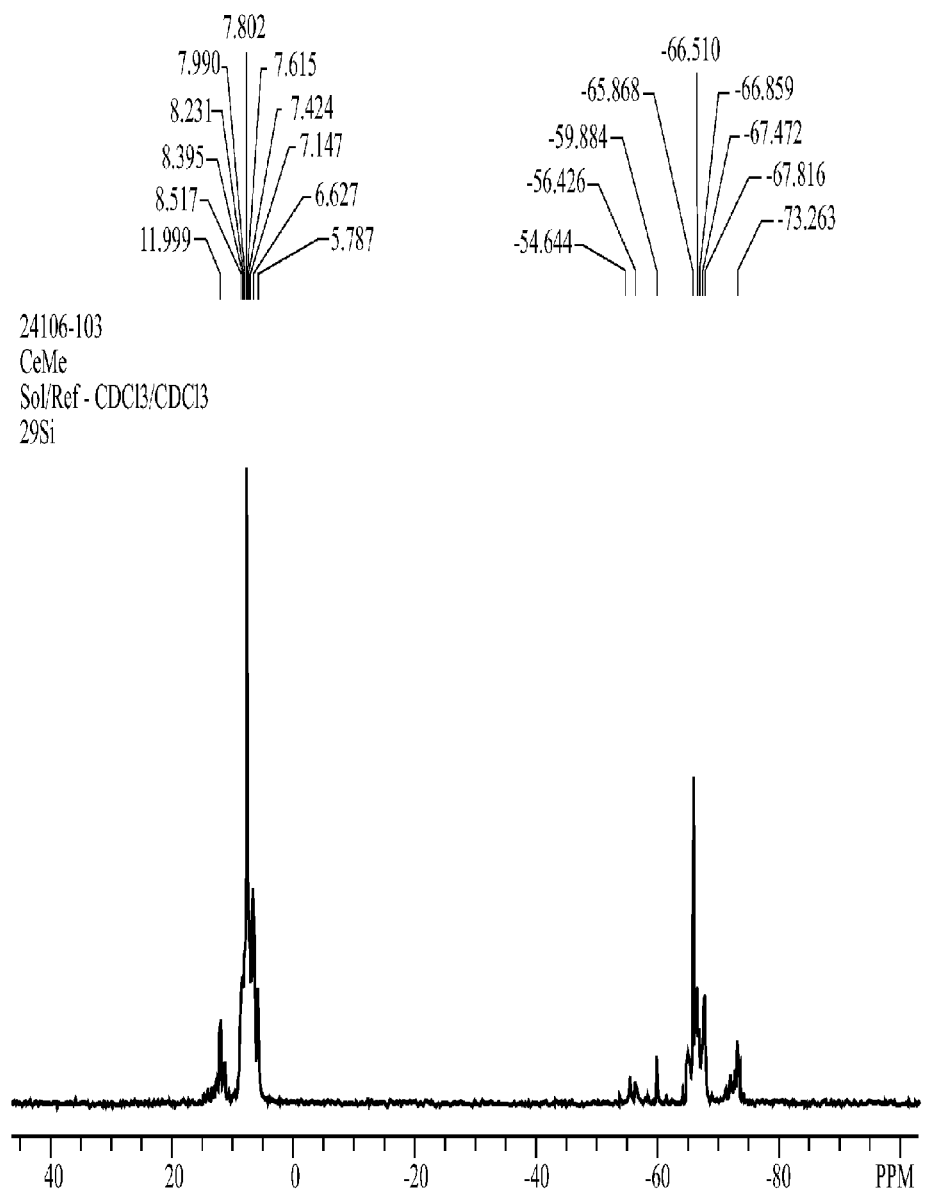
FIG. 3 is a $^{29}$Si NMR spectrograph of the compound of Structure I (i.e., tetrakis((1,1,1,3,5,5,5-heptamethyltrisiloxan-3-yl)oxy)cerium)
Figure 4:
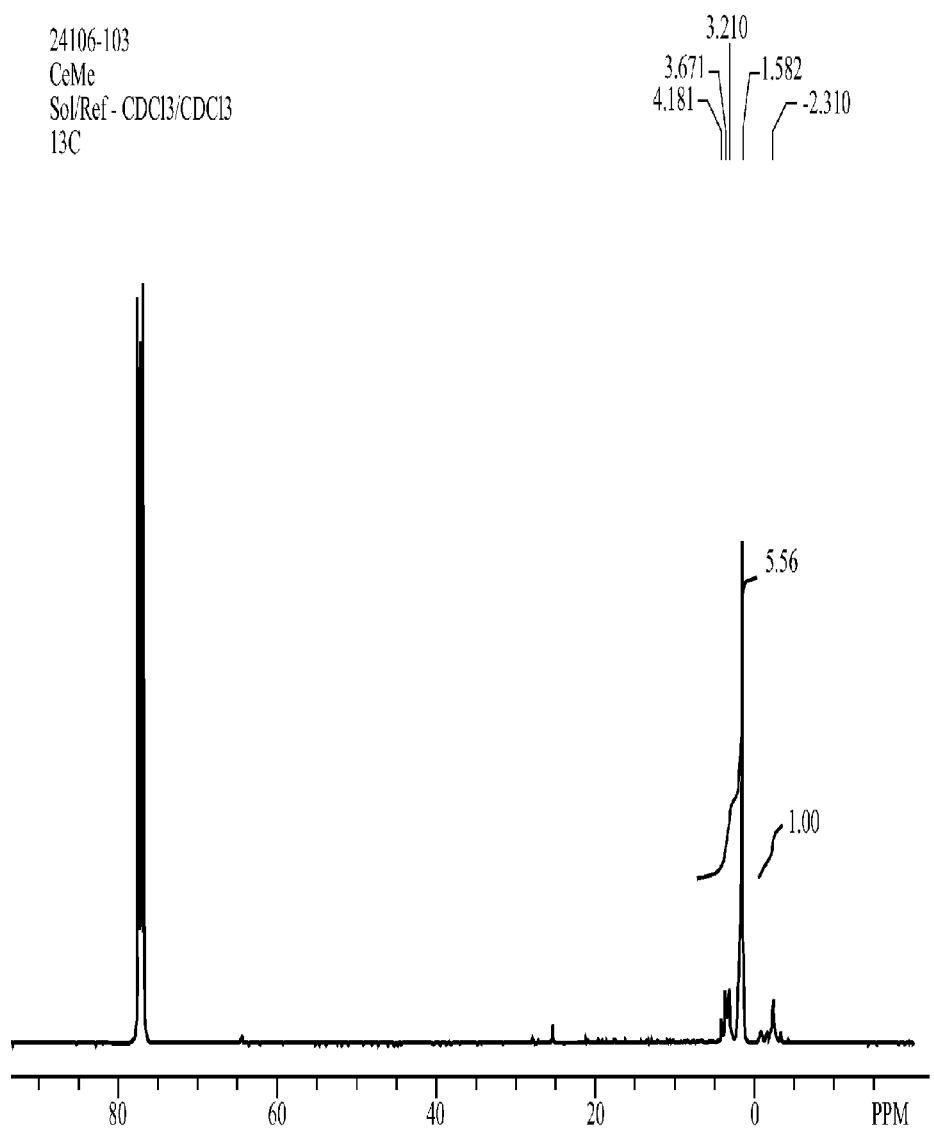
FIG. 4 is a $^{13}$C NMR spectrograph of the compound of Structure I.
Figure 5:
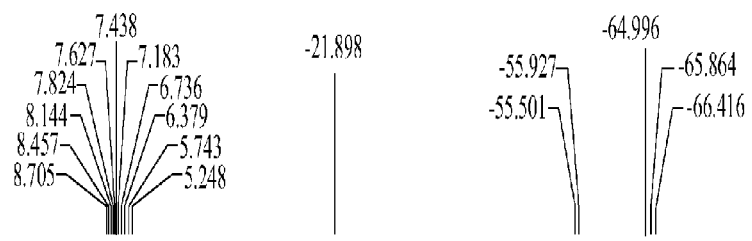
FIG. 5 is a $^{29}$Si NMR spectrograph of the compound of Structure III (i.e., tris((1,1,1,3,5,5,5-heptamethyltrisiloxan-3-yl)oxy)cerium)
Figure 5:
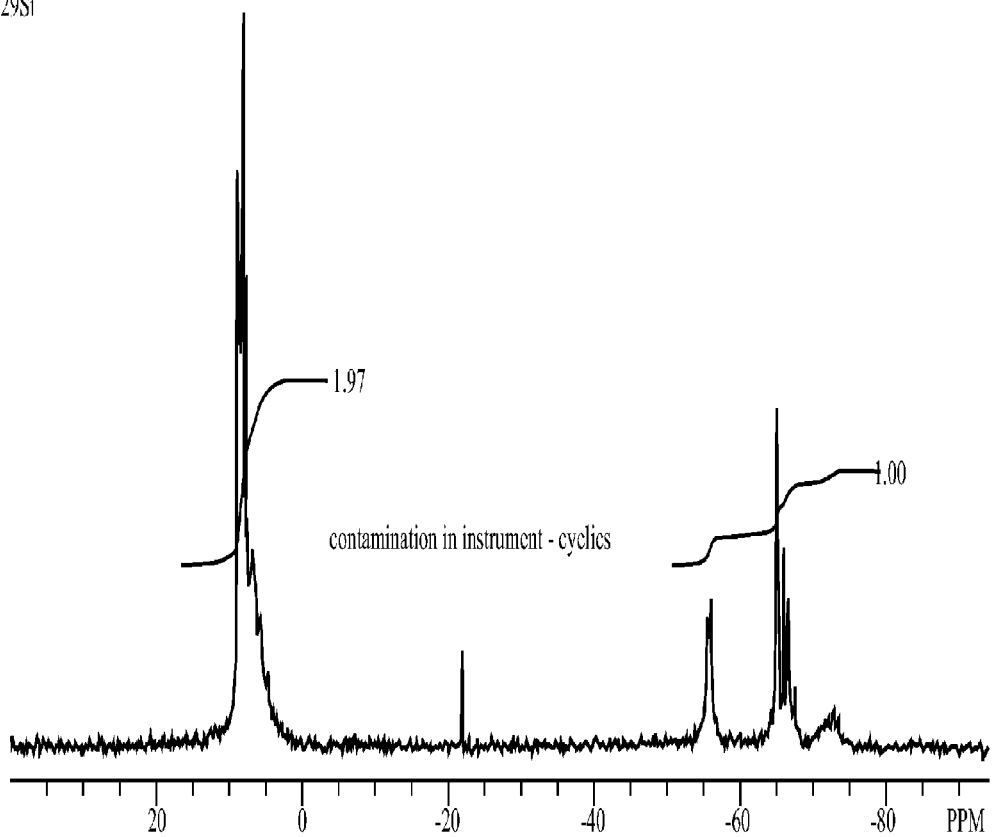
Figure 6:
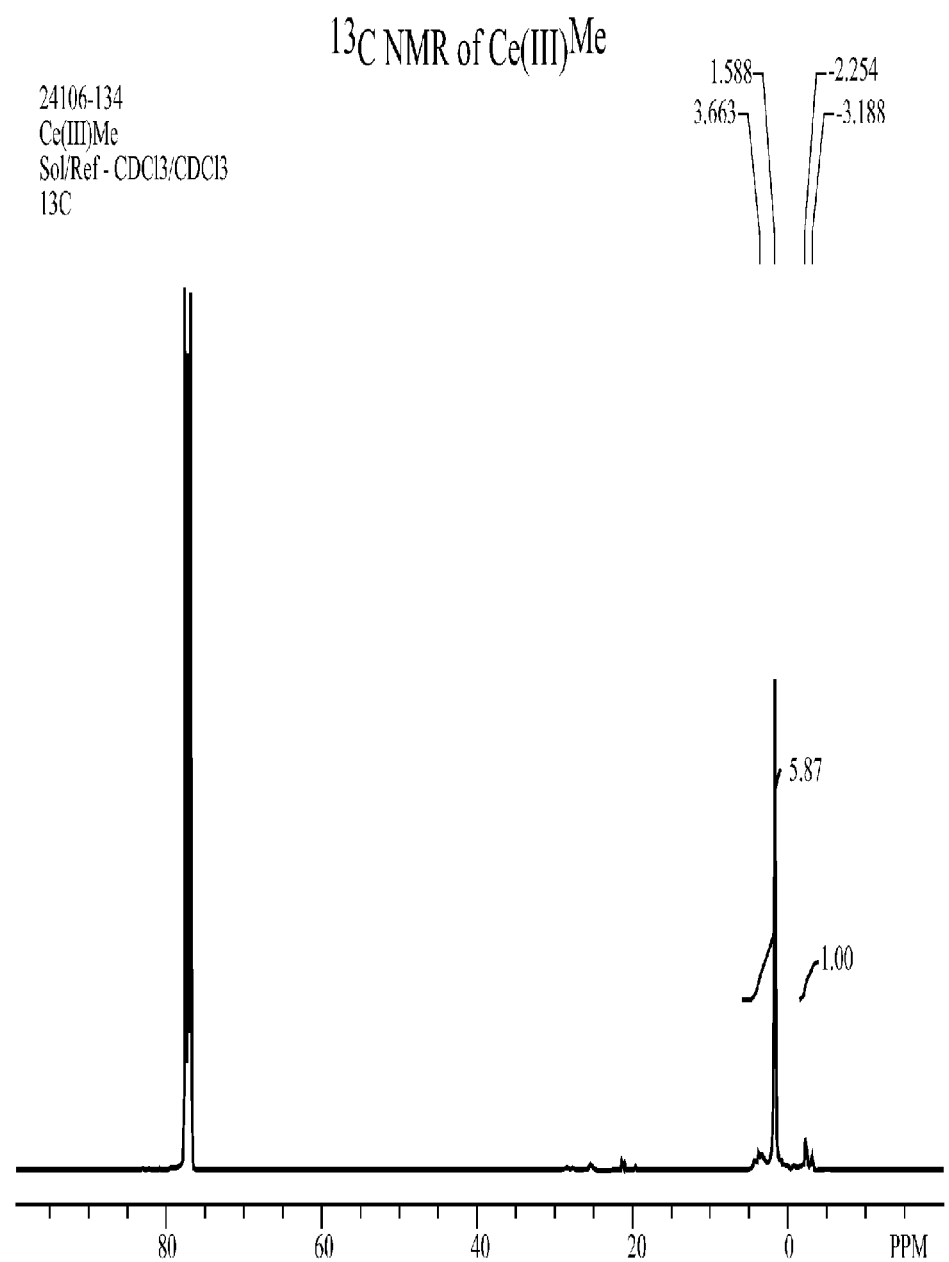
FIG. 6 is a $^{13}$C NMR spectrograph of the compound of Structure III.
Figure 7:
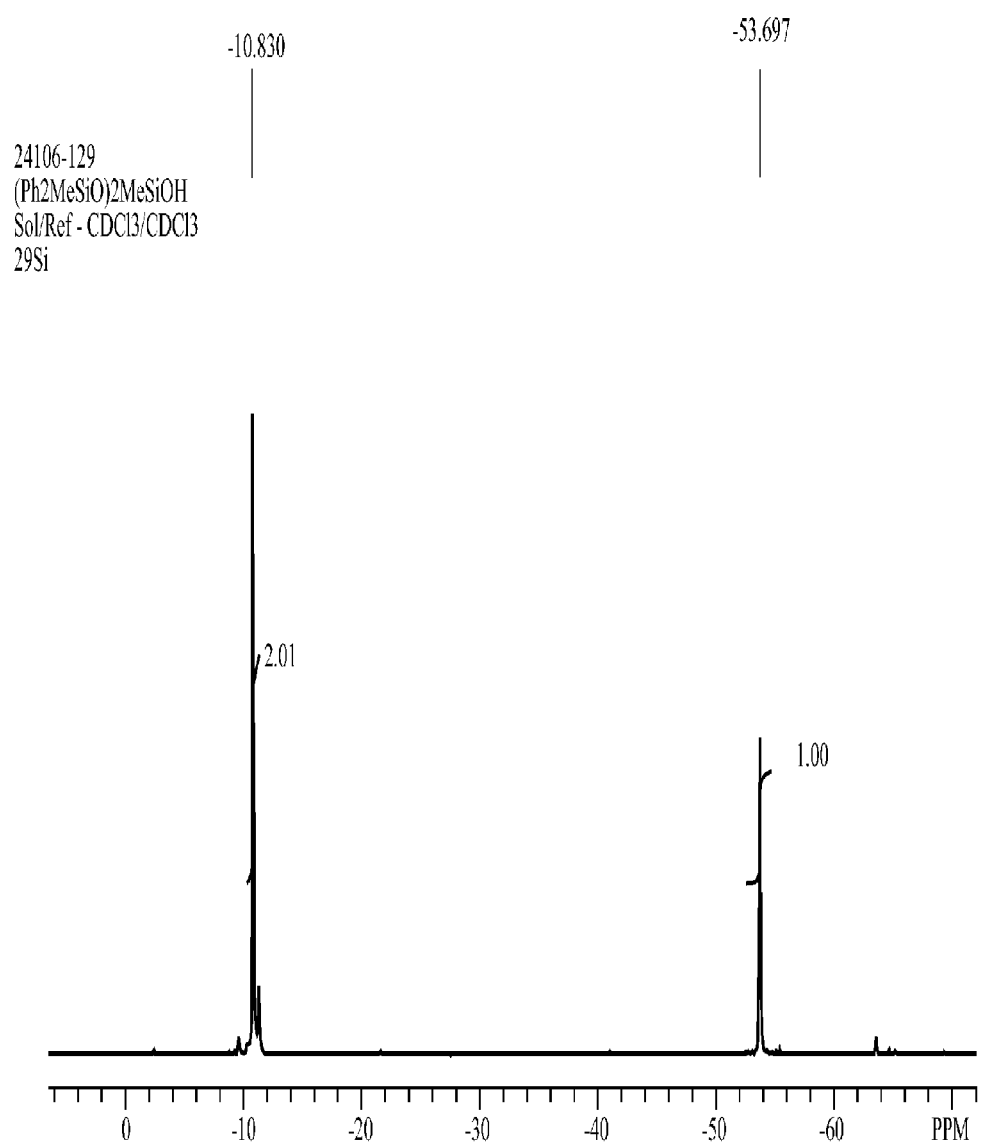
FIG. 7 is a $^{29}$Si NMR spectrograph of 1,3,5-trimethyl-1,1,5,5-tetraphenyltrisiloxan-3-ol.
Figure 8:
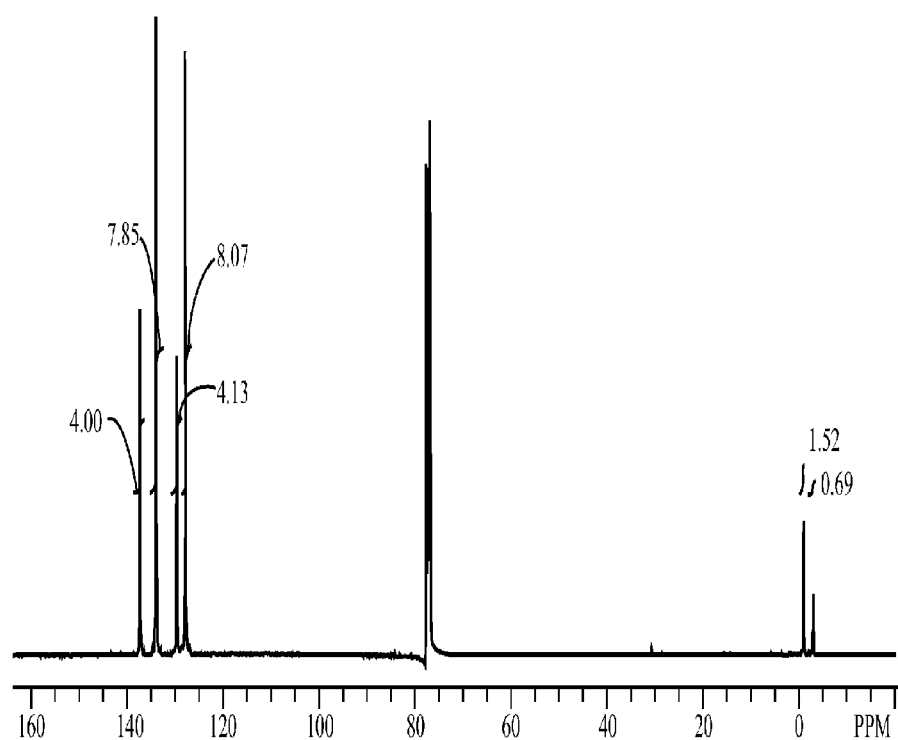
FIG. 8 is a $^{13}$C NMR spectrograph of 1,3,5-trimethyl-1,1,5,5-tetraphenyltrisiloxan-3-ol.
Figure 9:
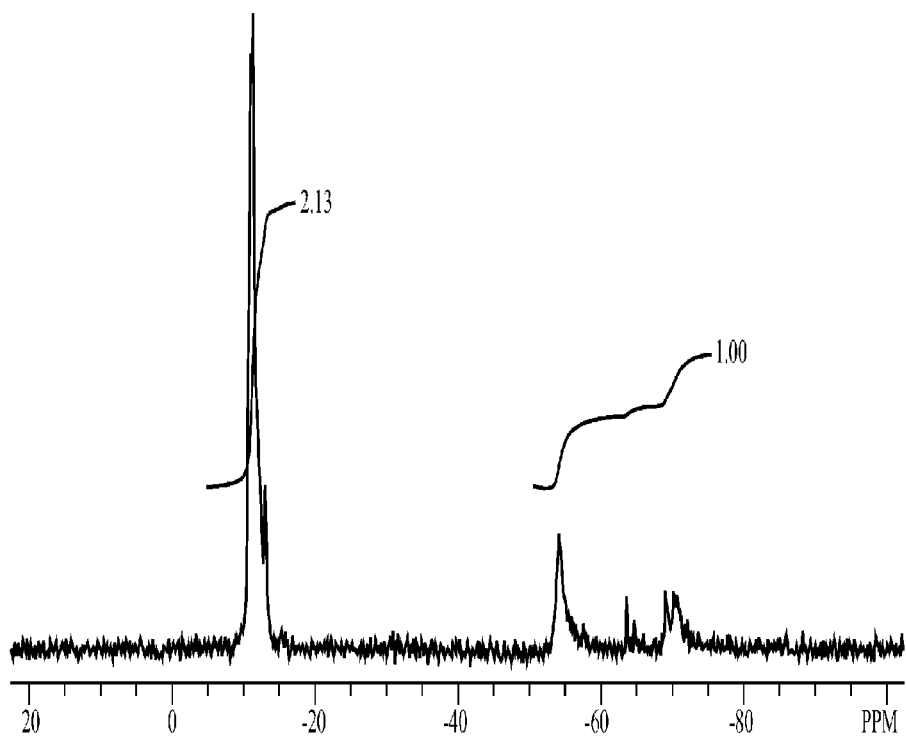
FIG. 9 is a $^{29}$Si NMR spectrograph of the compound of Structure II (i.e., tetrakis((1,3,5-trimethyl-1,1,5,5-tetraphenyltrisiloxan-3-yl)oxy)cerium)
Figure 10:
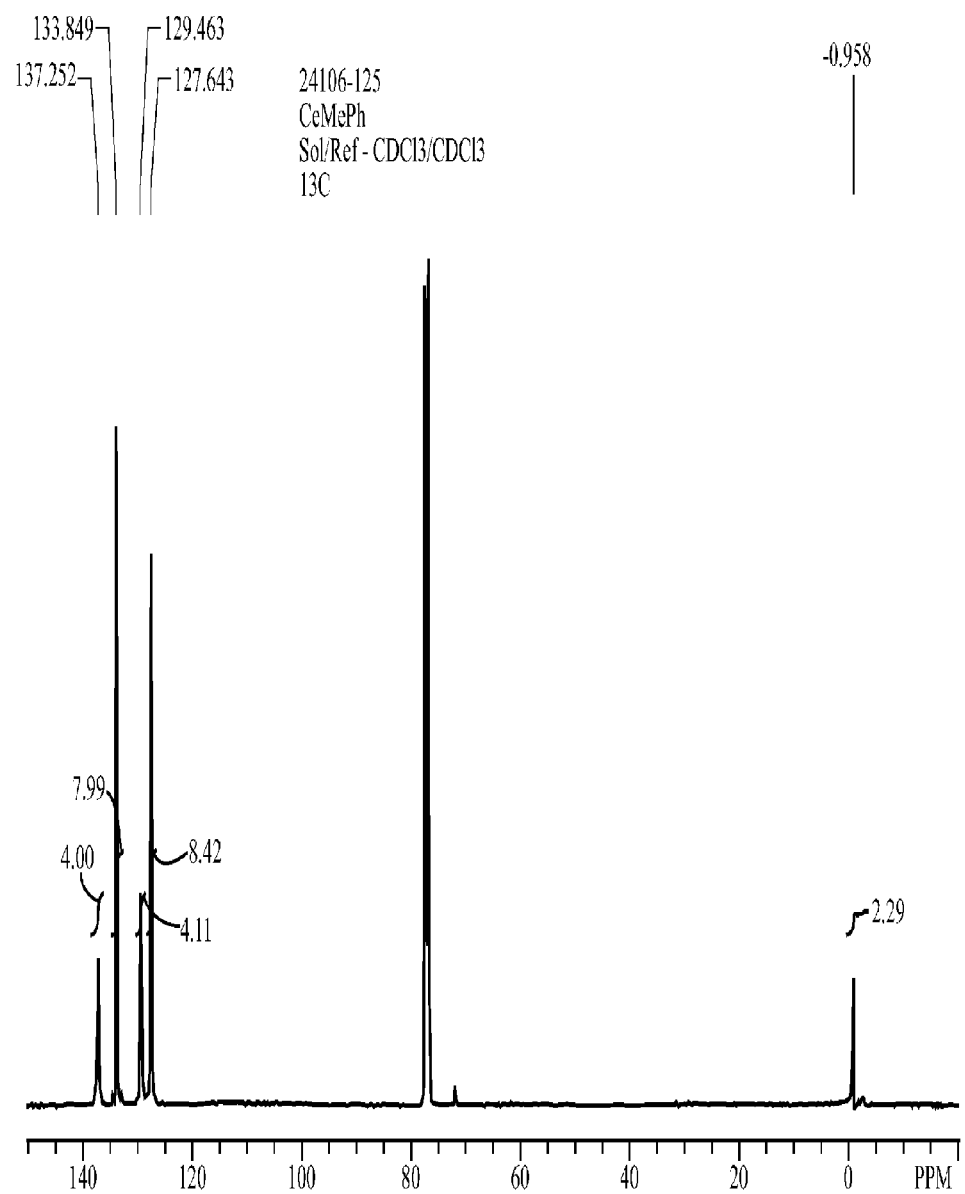
FIG. 10 is a $^{13}$C NMR spectrograph of the compound of Structure II.
Figure 11:
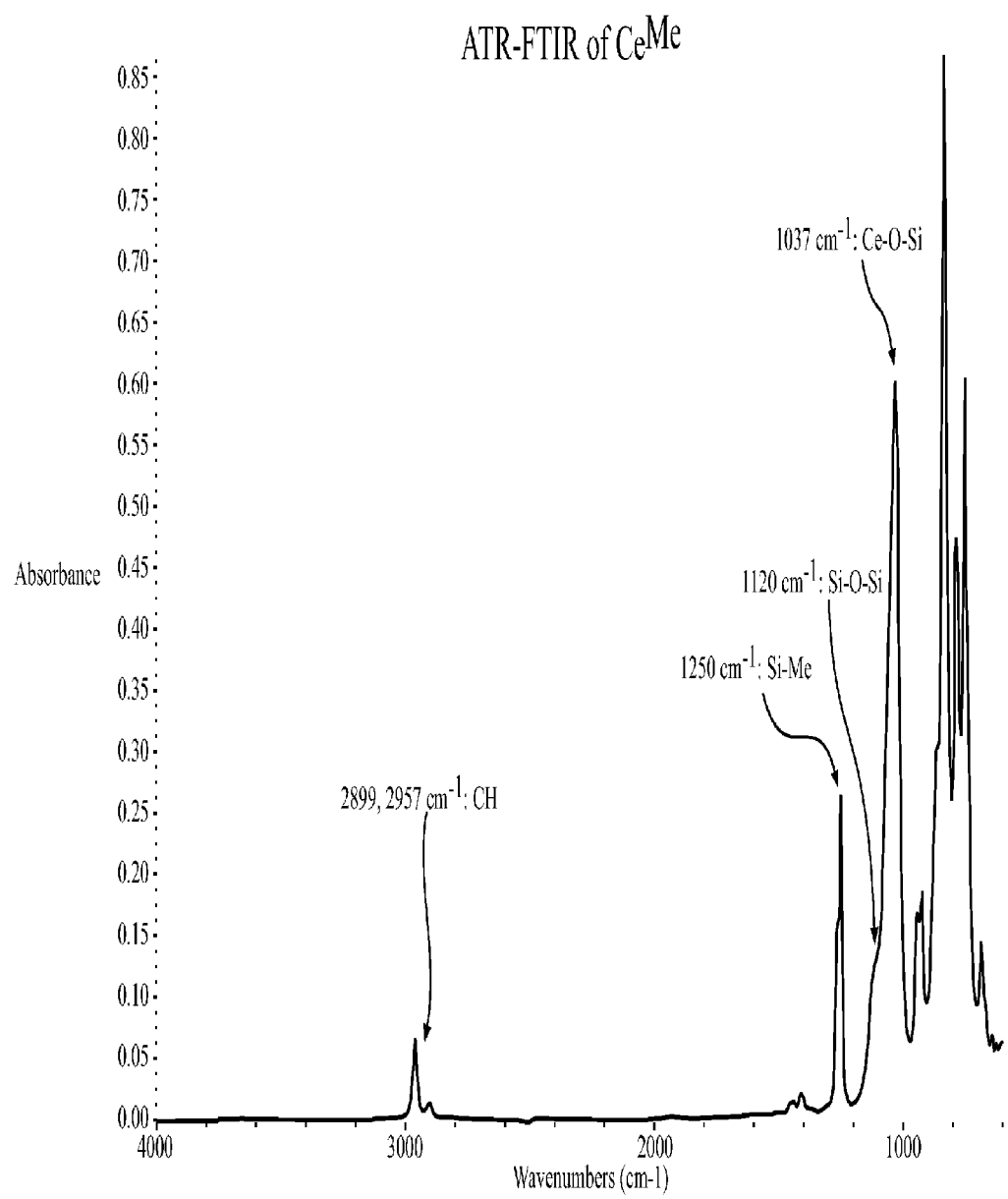
FIG. 11 is an ATR-FTIR spectrograph of the compound of Structure I.
Figure 12:
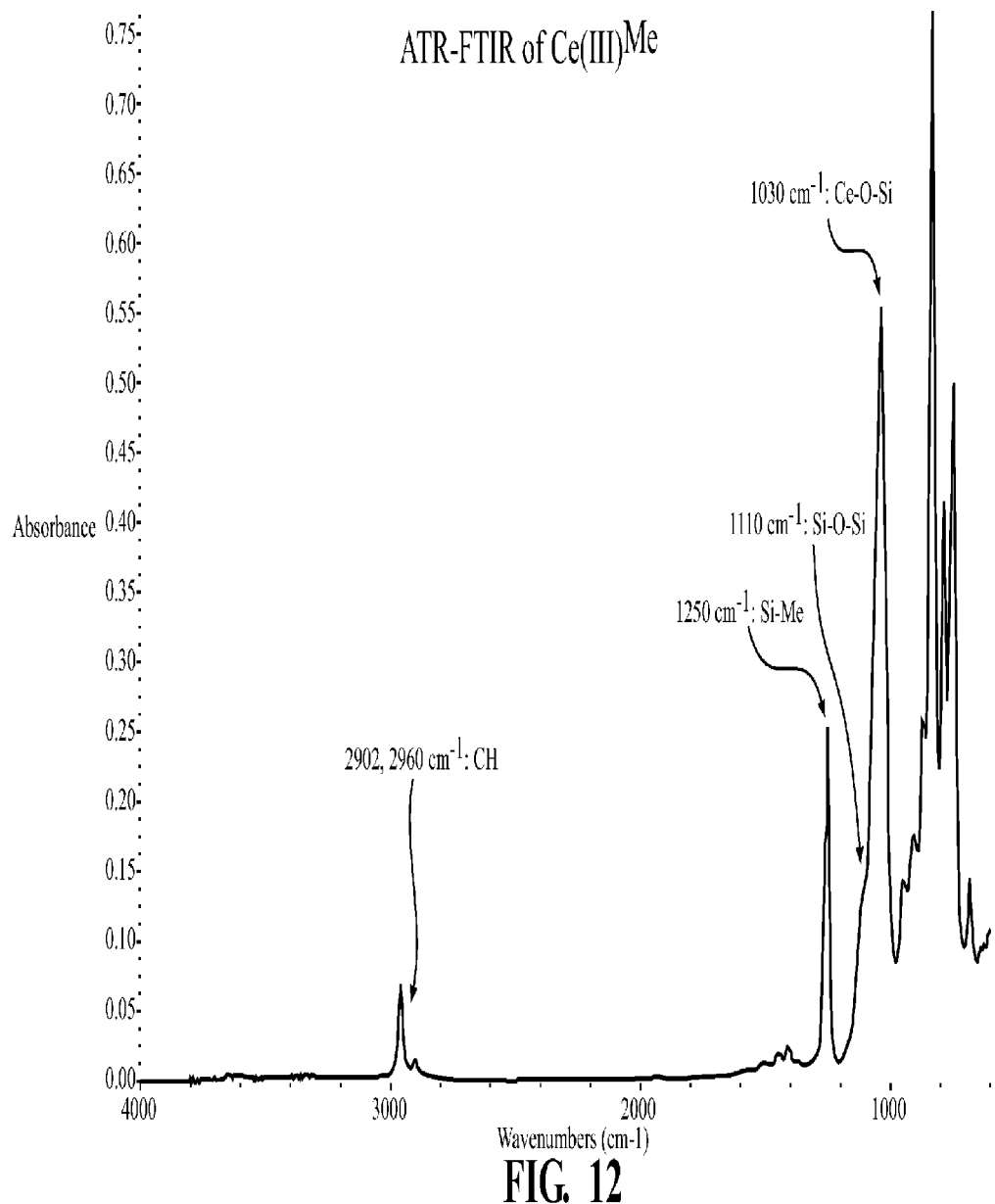
FIG. 12 is an ATR-FTIR spectrograph of the compound of Structure III.
Figure 13:
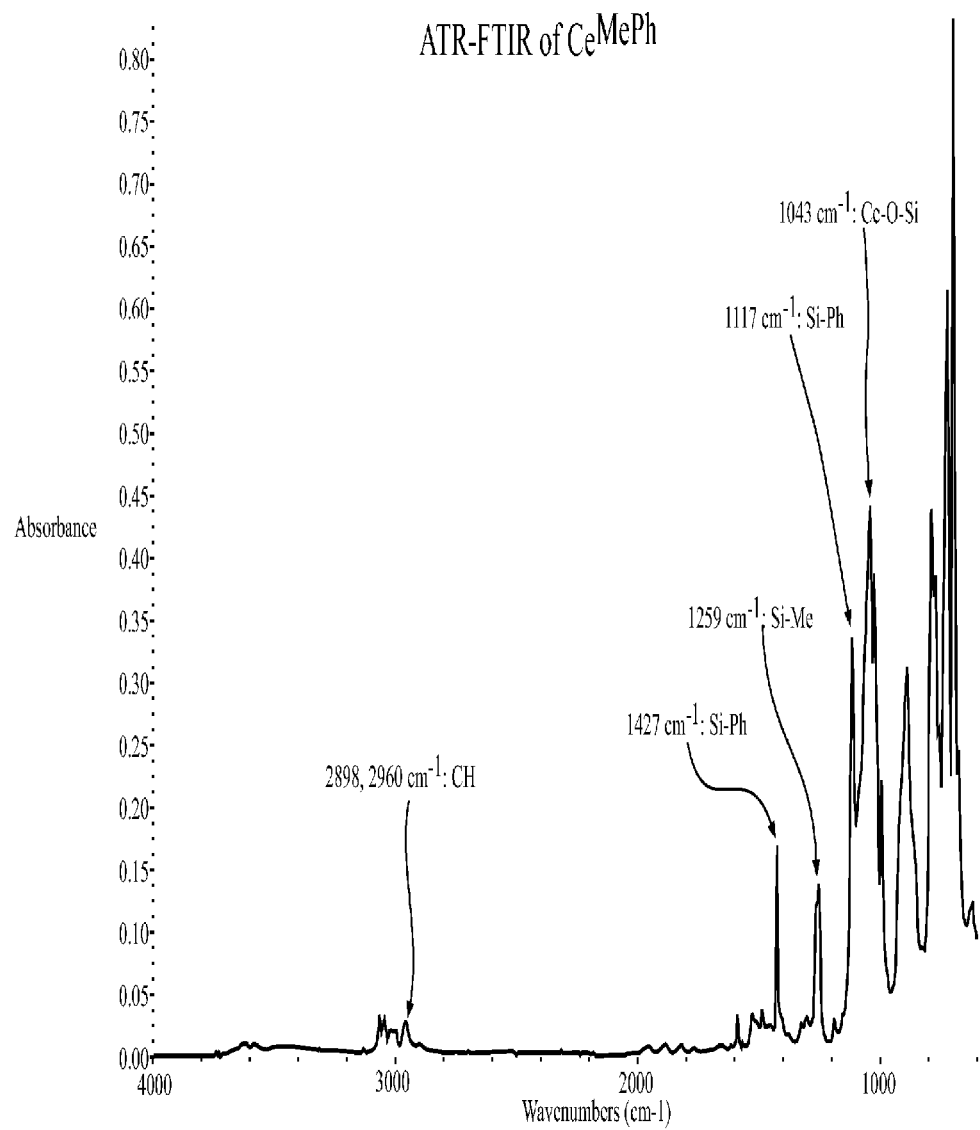
FIG. 13 is an ATR-FTIR spectrograph of the compound of Structure II.

The present disclosure provides an additive for a silicone encapsulant. The additive has the structure:

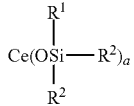

In this structure, subscript a is 3 or 4 which corresponds to the cerium in a 3+ (III) or 4+ (IV) oxidation state. In a 3+ state (III), cerium is typically bonded to three ligands, i.e., a=3. In the 4+ (IV) state, cerium is typically bonded to four ligands, i.e., a=4. The aforementioned OSi$R^1R^2R^3$ structure may be alternatively described as a (monodentate) ligand, e.g. a trifunctional siloxy ligand, which may also be described as a tertiary silanol ligand or a trisubstituted silanol ligand.

In addition, in the aforementioned structure, $R^1$ and $R^2$ are each —O—Si($R^4$)($R^5$)($R^6$). Non-limiting exemplary structures of the additive are set forth below. However, it is to be understood that any one or more of $R^4$, $R^5$, and/or $R^6$ may be in any location relative to the Si to which each is directly bonded.

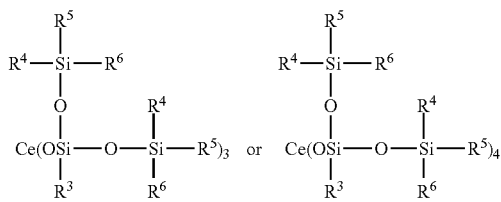

Each of $R^1$ and $R^2$ may be described as an "M" unit (e.g. $R_3SiO_{1/2}$ wherein R may be any one or more groups/moieties described herein), as is appreciated in the silicone arts, and each may be the same or may be different from one another. Each of $R^4$, $R^5$, and $R^6$ is independently chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups. In addition, $R^3$ is independently chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups. More specifically, each hydrocarbyl group may independently have 1, 2, 3, 4, 5, 6, 7, 8, 9, or 10 carbon atoms or any range of carbon atoms therebetween. Similarly, each alkyl group may independently have 1, 2, 3, 4, 5, 6, 7, 8, 9, or 10 carbon atoms, or any range of carbon atoms therebetween. In various embodiments, one or more alkyl groups is defined as a methyl group, ethyl group, propyl group, or butyl group. Each alkenyl group may independently have 2, 3, 4, 5, 6, 7, 8, 9, or 10 carbon atoms or any range of carbon atoms therebetween. In various embodiments, one or more alkenyl groups is defined as a vinyl group. Furthermore, each aryl group may independently have 6, 7, 8, 9, or 10 carbon atoms or any range of carbon atoms therebetween. In various embodiments, one or more aryl groups is further defined as a phenyl group.

In additional embodiments, at least 5, 10, 15, 20, 25, 30, 35, 40, 45, 50, 55, 60, 65, 70, 75, 80, 85, 90, 95, 96, 97, 98, or 99, mol percent of a total of the groups $R^3$-$R^6$ are methyl groups. In other embodiments, at least 5, 10, 15, 20, 25, 30, 35, 40, 45, 50, 55, 60, 65, 70, 75, 80, 85, 90, 95, 96, 97, 98, or 99, mol percent of a total of the groups $R^3$-$R^6$ are phenyl groups. It is contemplated that, in other embodiments, the aforementioned mol percent may describe each of $R^3$-$R^6$ considered individually and not as a whole. In still other embodiments, each of the groups $R^3$-$R^6$ may be a methyl group. Alternatively, each of the groups $R^3$-$R^6$ may be a phenyl group. Still further, in various embodiments, any three groups, e.g. each of $R^3$, $R^4$, and $R^6$, may be phenyl groups. In such embodiments, the structures may be as follows, or may be different:

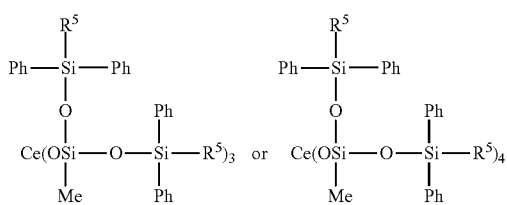

In an additional embodiment, the additive has the structure below (Structure (I)):

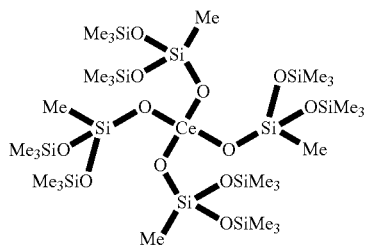

wherein a is 4 and Me is methyl. The aforementioned structure may be alternatively described as tetrakis((1,1,1,3,5,5,5-heptamethyltrisiloxan-3-yl)oxy)cerium having the chemical formula $C_{28}H_{84}CeO_{12}Si_{12}$.

In another embodiment, the additive has the structure below (Structure (II)):

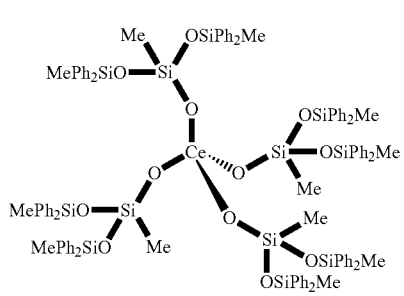

wherein a is 4, Me is methyl, and Ph is phenyl. The aforementioned structure may be alternatively described as tetrakis((1,3,5-trimethyl-1,1,5,5-tetraphenyltrisiloxan-3-yl)oxy)cerium having the chemical formula $C_{108}H_{116}CeO_{12}Si_{12}$. It is contemplated that additional embodiments may have the same chemical structure but different stereochemistry.

In still another embodiment, the additive has the structure below (Structure (III)):

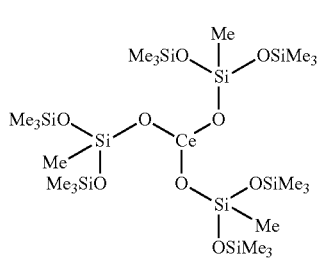

wherein a is 3 and Me is methyl. The aforementioned structure may be alternatively described as tris((1,1,1,3,5,5,5-heptamethyltrisiloxan-3-yl)oxy)cerium having the chemical formula $C_{21}H_{63}CeO_9Si_9$.

It is contemplated that the aforementioned structures may be simplified structures. For example, in one embodiment, the generic structure may be written as [Cerium(OSiR$_3$)$_n$]$_x$ where x is the degree of molecular complexity. In one embodiment, the value of x does not matter because the empirical formula (or the ratio of Cerium:Si) remains unchanged.

Physical Properties of the Additive:

The additive is not limited to having any particular physical properties so long as the structure is as described above. The additive may have a density of from 0.95 to 1.20, from 1.00 to 1.15, or from 1.05 to 1.10, g/cm³, or any value or range of values therebetween. In addition, the additive may be described as being free of, or including less than 5, 4, 3, 2, 1, 0.5, 0.1, or 0.05 weight percent of, an alkaline earth metal salt or alkaline metal salt.

In other embodiments, the additive is soluble in an organofunctional silicone. The terminology "soluble in" typically describes that up to 50, 45, 40, 35, 30, 25, 20, 15, 10, 5, 4, 3, 2, or 1, grams of the additive may be soluble in 50, 55, 60, 65, 70, 75, 80, 85, 90, 95, 96, 97, 98, or 99 grams of the organofunctional silicone, respectively. Alternatively, the organofunctional silicone may be soluble in the additive. In such embodiments, for example, the terminology "soluble in" typically describes that up to 50, 45, 40, 35, 30, 25, 20, 15, 10, 5, 4, 3, 2, or 1, grams of the organofunctional silicone may be soluble in 50, 55, 60, 65, 70, 75, 80, 85, 90, 95, 96, 97, 98, or 99 grams of the additive, respectively. Typically, a determination of "solubility" is determined visually when the additive and the organofunctional silicone are combined as no phase separation is seen by the naked eye. However, solubility may alternatively be assessed by one or more standardized (e.g. ASTM) tests, as appreciated in the silicone arts.

For example, the additive may be deemed to be soluble in the organofunctional silicone or vice versa, when, the combination consisting of the two, i.e., the additive and the organofunctional siloxane, shows no visible signs of inhomogeneity (e.g. settling or non-uniform phase separation) after 24 hours at room temperature. The organofunctional silicone described above may be the same as the polyorganosiloxane that will be described in greater detail below, may be a silicone fluid, e.g. Dow Corning 200 fluid, polydimethylsiloxane, or a phenyl substituted siloxane such as Dow Corning 510 fluid.

In additional embodiments, the additive includes 1 to 20, 5 to 20, 6 to 20, 10 to 20, 15 to 20, 5 to 10, 10 to 15, 5 to 15, 3 to 25, 1, 2, 3, 4, 5, 6, 7, 8, 9, 10, 11, 12, 13, 14, 15, 16, 17, 18, 19, 20, 21, 22, 23, 24, or 25, weight percent of cerium based on a total weight of the additive, or any value or range of values therebetween. The weight percent of cerium is typically determined by the chemical structure of the additive itself. For example, Structure (I) above includes 12.85 to 12.9 weight percent of cerium. Structure (II) above includes 4.2 to 6.73 weight percent of cerium. Structure (III) above includes 16.43 to 21.0 weight percent of cerium.

In other embodiments, the additive may be alternatively described as a cluster, e.g. a cerium silyloxide cluster. For example, individual molecules of the additive, having the general structure described above, may cluster together via covalent bonds or intermolecular forces. For example, the additive may cluster into groups of 2, 3, 4, 5, 6, 7, 8, 9, or 10, or even more, units or individual additive molecules. Non-limiting examples of these clusters may have the following formula wherein n is a number as set forth immediately above or any range of numbers therebetween:

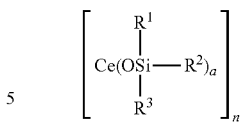

It is also contemplated that the additive could be complexed with a neutral donor ligand via a dative interaction. In some embodiments the additive is further complexed with the neutral donor ligand, and in other embodiments is not complexed with and lacks the neutral donor ligand. Examples of neutral donor ligands can include but are not limited to, amines (e.g. pyridine, triethylamine, $NH_3$), ethers (e.g. tetrahydrofuran, dioxane, diethylether), alkenes/alkynes (e.g. ethylene, acetylene), aromatics (e.g. benzene, toluene), alcohols (e.g. ethanol, phenol), silanols (e.g. excess $HOSi(R^1)(R^2)(R^3)$, trimethylsilanol), phosphines (e.g. tricyclohexylphosine, triphenylphosphine), thiols (e.g. decylmercaptan), etc. It is also contemplated that more than one of these species may be simultaneously present in the interaction or in any combination from the non-limiting list of donor ligands. Typically these ligands include a heteroatom such as N, O, P, S, or As, Se, Te, B, etc. These types of ligands can be used to break up the aforementioned clusters. In addition, it is contemplated that the additive may include one or more bidentate and/or tridentate ligands that contain one or multiple silanol attachment points to the exclusion of the monodentate ligands described above, e.g. so long as the M-O—$Si(R^1)(R^2)(R^3)$ ligand is present. If there are multiple attachment points on the ligand, a high molecular weight cluster may be formed.

Reaction Products:

In one embodiment, the additive is described as a reaction product of a reaction of cerium alkoxide and a hydroxyl functional organosiloxane. Said differently, in this embodiment, the additive results from, or is the product of, the reaction of the cerium alkoxide and the hydroxyl functional organosiloxane. The cerium alkoxide is not particularly limited. In various embodiments, the cerium alkoxide is further defined as $Ce(O—R)_{3 \text{ or } 4}$, corresponding to cerium (III) or cerium (IV), as is appreciated in the art. Each R ($R^4$, $R^5$, $R^6$) may be independently chosen from $C_1$-$C_{10}$ hydrocarbyl groups, $C_1$-$C_{10}$ alkyl groups, $C_2$-$C_{10}$ alkenyl groups, and $C_6$-$C_{10}$ aryl groups. These hydrocarbyl, alkyl, alkenyl, and aryl groups, and the corresponding numbers of carbon atoms therein, may be as described above. This reaction may proceed as set forth below:

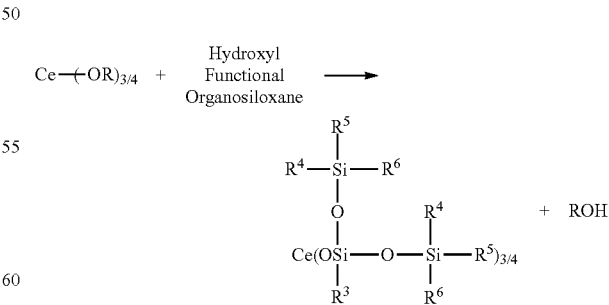

wherein the cerium of both the alkoxide and the additive may be cerium (III) or (IV). The hydroxyl functional organosiloxane may be utilized in a molar ratio of 3:1 or 4:1, e.g. in at least a 3:1 molar ratio when a cerium (III) compound or cerium metal is utilized or at least a 4:1 molar ratio when a cerium (IV) compound or cerium metal is utilized. Alternatively, the hydroxyl functional organosiloxane may be utilized in molar excess.

In another embodiment, the additive is further defined as a reaction product of a reaction of cerium ammonium nitrate and a hydroxyl functional organosiloxane. Said differently, in this embodiment, the additive results from, or is the product of, the reaction of the cerium ammonium nitrate and the hydroxyl functional organosiloxane. Just as above, the cerium ammonium nitrate is not particularly limited and may be cerium (III) ammonium nitrate, cerium (IV) ammonium nitrate, or a combination thereof. This reaction may proceed as set forth in one or more of the reactions below wherein each of $R^4$, $R^5$, and $R^6$ is as described above:

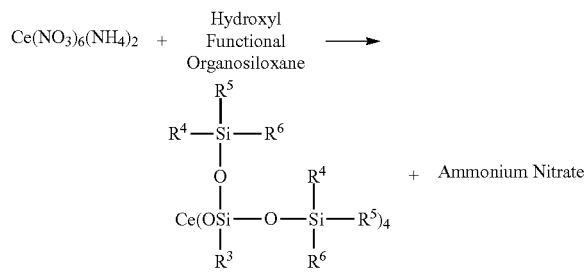

;(which can also be written as below)

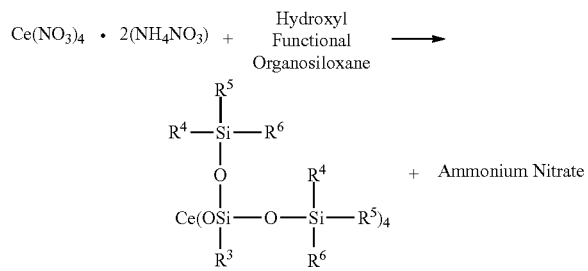

;and/or a reaction below

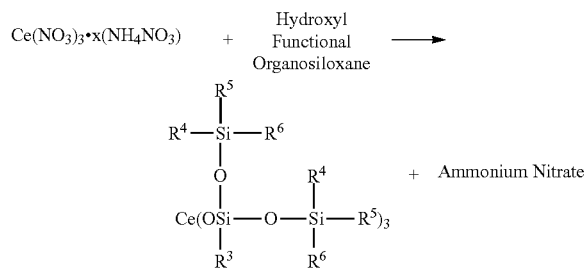

wherein x is 1-3. Each of these reactions are written as non-stoichiometric reactions and typically require the presence of dissolved $NH_3$ in solvent and/or the presence of an $NH_3$ atmosphere.

In still another embodiment, the additive is further defined as a reaction product of a reaction of cerium metal, i.e., cerium (0), and a hydroxyl functional organosiloxane. Said differently, in this embodiment, the additive results from, or is the product of, the reaction of the cerium metal and the hydroxyl functional organosiloxane. This reaction may proceed as set forth below wherein each of $R^4$, $R^5$, and $R^6$ is as described above:

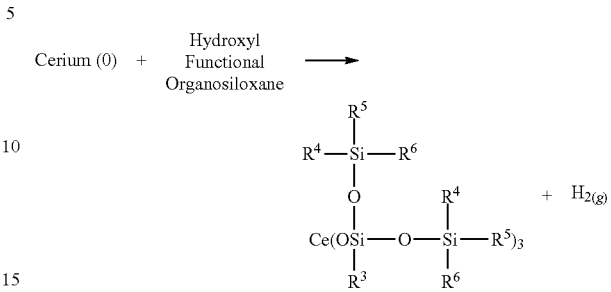

In another embodiment, the additive is further defined as an exchange reaction product of a reaction of a trifunctional silyloxy cerium (III) or (IV) compound and a hydroxyl functional organosiloxane. Said differently, in this embodiment, the additive is the result of, or the product of, the exchange of silicon atoms and/or entire ligands (from an exchange reaction) of the trifunctional silyloxy cerium (III) or (IV) compound and the hydroxyl functional organosiloxane. This reaction may proceed as set forth below wherein each of $R^4$, $R^5$, and $R^6$ is as described above:

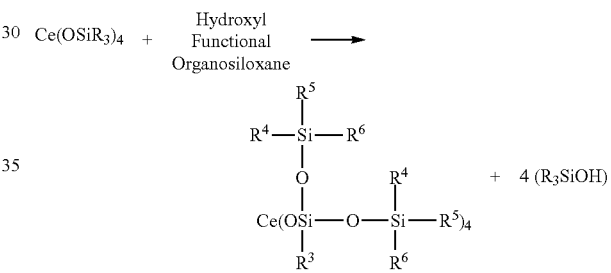

wherein R may be any group as described above or below and the silanol produced is different from the hydroxyl functional organosiloxane.

Hydroxyl Functional Organosiloxane:

The hydroxyl functional organosiloxane as described above is not particularly limited. In one embodiment, the hydroxyl functional organosiloxane has the formula $M^1D^{R,}$ $_{OH}M^2$. In this formula, R may be any group described above or below. Also in this embodiment, the nomenclature "M" and "D" represent an "M unit" and a "D" unit (e.g. $R_2SiO_{2/2}$ wherein R may be any one or more groups/moieties described herein), respectively, as appreciated in the silicone arts. Similarly, the nomenclature R,OH describes that the silicon atom of the D unit is bonded to an R group and also to an OH group. In one embodiment, each of $M^1$ and $M^2$ independently have the formula $O—Si(R^4)(R^5)(R^6)$, wherein $R^4$, $R^5$, and $R^6$ are as described above. $M^1$ and $M^2$ may be the same or may be different. In various embodiments, the hydroxyl functional organosiloxane has one or more of the structures:

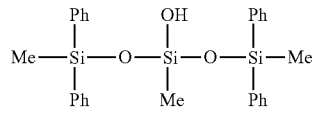

-continued

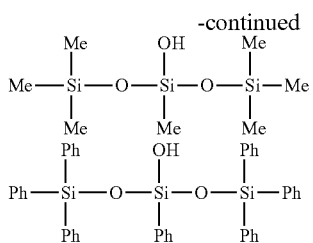

wherein Me is methyl and Ph is phenyl. It is contemplated that a single hydroxyl functional organosiloxane, or two or more hydroxyl functional organosiloxanes may be utilized.

The hydroxyl functional organosiloxane may be formed by any method known in the art. For example, the hydroxyl functional organosiloxane may be formed by a method that includes one or more steps as described immediately below:

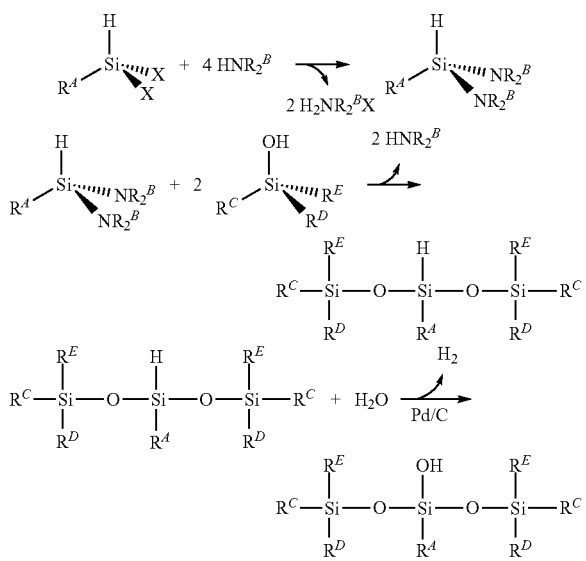

$R^B$ = Me, Et, alk, Ph, etc
X = Cl, Br, I
$R^A = R^C$ = Me
$R^D = R^E$ = Ph

Method of Making the Additive:

This disclosure also provides a method of making the additive. The additive may be formed by any method in the art. Similarly, the method may include any of the reactions described above. Typically, the additive is formed such that no (or less than 5, 4, 3, 2, 1, 0.5, 0.1, or 0.05 weight percent of an alkaline earth metal salt or alkaline metal salt) is formed in the process. In other words, the additive is typically free of, or includes less than 5, 4, 3, 2, 1, 0.5, 0.1, or 0.05 weight percent of an alkaline earth metal salt or alkaline metal salt.

In one embodiment, the method includes the step of reacting cerium metal or a cerium (III) or (IV) compound with the hydroxyl functional organosiloxane. The hydroxyl functional organosiloxane may be utilized in a molar ratio of 3:1 or 4:1, e.g. in at least a 3:1 molar ratio when a cerium (III) compound or cerium metal is utilized or at least a 4:1 molar ratio when a cerium (IV) compound or cerium metal is utilized. Alternatively, the hydroxyl functional organosiloxane may be utilized in molar excess. Just as above, the cerium (III) or (IV) compound may be any of the compounds described above.

In one embodiment, the method produces an alcohol and the method further comprises the step of separating the alcohol from the additive. Typically, the alcohol (represented above as ROH) may be any known in the art. However, the alcohol typically includes an R group from the cerium alkoxide. The alcohol may be removed from the additive by any means known in the art, including distillation. Alternatively, this step may be described as removing the additive from the alcohol, e.g. depending on temperature of distillation. It is contemplated that the alcohol may not be removed.

In another embodiment, the cerium (III) or (IV) compound is further defined as cerium ammonium nitrate. In a related embodiment, the method produces ammonium nitrate and the method further comprises the step of separating the ammonium nitrate from the additive. The cerium ammonium nitrate is typically represented by one or more of the following formulae:

$Ce(NO_3)_6(NH_4)_2$ $Ce(NO_3)_4.2(NH_4NO_3)$
$Ce(NO_3)_3$ $x(NH_4NO_3)$

In addition, the ammonium nitrate may be removed from the additive by any means known in the art, including filtration. Alternatively, this step may be described as removing the additive from the ammonium nitrate. It is contemplated that the ammonium nitrate may not be removed.

In a further embodiment, the cerium metal (i.e., cerium (0)) is utilized. In this embodiment, the method step is further defined as reacting the cerium metal with the hydroxyl functional organosiloxane. This reaction may occur in the presence of ammonia gas and may generate hydrogen gas. The hydrogen gas may be removed or evacuated by any method of the art. It is contemplated that the hydrogen gas may not be removed.

In still another embodiment, the cerium (III) or (IV) compound is further defined as a trifunctional siloxy cerium compound and the step of reacting is further defined as reacting via an exchange reaction. The exchange reaction typically forms a silanol that is different from the hydroxyl functional organosiloxane. The silanol may be removed from the additive by any means known in the art, including distillation. Alternatively, this step may be described as removing the additive from the silanol, e.g. depending on temperature of distillation. It is contemplated that the silanol may not be removed.

In other embodiments, cerium (IV) additives can be formed by one or more of the following reactions/equations:

$Ce(OR)_4 \cdot ROH + 4 R_3SiOH \rightarrow Ce(OSiR_3)_4 + 5 ROH$ $Ce(OSiMe_3)_4 + 4 R_3SiOH \rightarrow Ce(OSiR_3)_4 + 4 Me_3SiOH$ $Ce(NO_3)_6(NH_4)_2 + 4 R_3SiOH + 4 NH_3 \rightarrow Ce(OSiR_3)_4 + 6 NH_4NO_3$ $Ce(NO_3)_6(NH_4)_2 + 6$ (Alkaline/Alkaline Earth) $OSiR_3 \rightarrow Ce(OSiR_3)_4 + 6$ (Alkaline/Alkaline Earth)$NO_3 + 2 R_3SiOH + 2 NH_3$ wherein R may be any of the groups described above.

In still other embodiments, cerium (III) additives can be formed by one or more of the following reactions/equations:

$CeX_3 + 3$ (Alkaline/Alkaline Earth)$OSiR_3 \rightarrow Ce(OSiR_3)_3 + 3$ (Alkaline/Alkaline Earth)$X$ $Ce(OR)_3 \cdot ROH + 3 R_3SiOH \rightarrow Ce(OSiR_3)_3 + 4 ROH$ $Ce(OSiMe_3)_3 + 3 R_3SiOH \rightarrow Ce(OSiR_3)_3 + 3 Me_3SiOH$ $Ce(N(SiMe_3)_2)_3 + 3 R_3SiOH \rightarrow Ce(OSiR_3)_3 + 3$ HMDZ Ce+3 R$_3$SiOH (in the presence of NH$_3$)→
  Ce(OSiR$_3$)$_3$+1.5 H$_2$ Ce(NO$_3$)$_5$(NH$_4$)$_2$+3 R$_3$SiOH+3 NH$_3$→Ce(OSiR$_3$)$_3$+5
  NH$_4$NO$_3$ Ce(NO$_3$)$_5$(NH$_4$)$_2$+5 (Alkaline/Alkaline Earth)
  OSiR$_3$→Ce(OSiR$_3$)$_3$+5 (Alkaline/Alkaline
  Earth)NO$_3$+2 R$_3$SiOH+2 NH$_3$ Wherein X is Cl, Br, or I and R is any group described above. As described above relative to cerium (III) and (IV) additives, the terminology "Alkaline/Alkaline Earth" describes an alkaline or alkaline earth metal such as Na/K, Rb or Mg/Ca/Sr, respectively. Typically, Na or K is utilized.

In still further embodiments, cerium (IV) additives, such as Structure II above, can be formed by the following reaction:

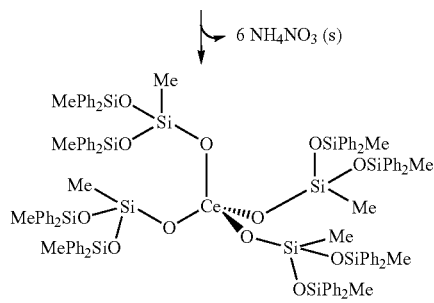

wherein a is 4, Me is methyl, and Ph is phenyl. It is contemplated that additional embodiments may have the same chemical structure but different stereochemistry.

Silicone Encapsulant:

This disclosure also provides a silicone encapsulant. The silicone encapsulant can be alternatively described as a polyorganosiloxane encapsulant wherein the terminology "silicone" includes or is a polymeric or oligomeric siloxane. The terminology "silicone" may be used interchangeably with polyorganosiloxane or may describe a specific compound, such as a silicone rubber, e.g. that may or may not be curable. The silicone encapsulant includes the additive and also a silicone, a polyorganosiloxane, or a polyorganosiloxane composition that itself includes one or more silicones or polyorganosiloxanes. The additive and the silicone, polyorganosiloxane, or a polyorganosiloxane composition that itself includes one or more silicones or polyorganosiloxanes, may be present in a combination, mixture, or admixture.

Typically, the additive is present in the encapsulant in an amount such that the cerium is present in an amount of from 5 to 1000 parts by weight per one million parts by weight (ppm) of the encapsulant. In various embodiments, the additive is present in amounts such that the cerium is present in an amount from 5 to 995, from 10 to 90, 15 to 985, 20 to 980, 25 to 975, 30 to 970, 35 to 965, 40 to 960, 45 to 955, 50 to 950, 55 to 945, 60 to 940, 65 to 935, 70 to 930, 75 to 925, 80 to 920, 85 to 915, 90 to 910, 95 to 905, 100 to 900, 105 to 895, 110 to 890, 115 to 885, 120 to 880, 125 to 875, 130 to 870, 135 to 865, 140 to 860, 145 to 855, 150 to 850, 155 to 845, 160 to 840, 165 to 835, 170 to 830, 175 to 825, 180 to 820, 185 to 815, 190 to 810, 195 to 805, 200 to 800, 205 to 795, 210 to 790, 215 to 785, 220 to 780, 225 to 775, 230 to 770, 235 to 765, 240 to 760, 245 to 755, 250 to 750, 255 to 745, 260 to 740, 265 to 735, 270 to 730, 275 to 725, 280 to 720, 285 to 715, 290 to 710, 295 to 705, 300 to 700, 305 to 695, 310 to 690, 315 to 685, 320 to 680, 325 to 675, 330 to 670, 335 to 665, 340 to 660, 345 to 655, 350 to 650, 355 to 645, 360 to 640, 365 to 635, 370 to 630, 375 to 625, 380 to 620, 385 to 615, 390 to 610, 395 to 605, 400 to 600, 405 to 595, 410 to 590, 415 to 585, 420 to 580, 425 to 575, 430 to 570, 435 to 565, 440 to 560, 445 to 555, 450 to 550, 455 to 545, 460 to 540, 465 to 535, 470 to 530, 475 to 525, 480 to 520, 485 to 515, 490 to 510, or 495 to 505, parts by weight per one million parts by weight (ppm) of the encapsulant. It is contemplated that, in additional embodiments, the additive may be present in the encapsulant such that the cerium is present in any amount or range of amounts therebetween any value(s) set forth above.

The silicone encapsulant is not particularly limited relative to physical properties. In various embodiments, the silicone encapsulant has a) a translucent to optically clear appearance, b) some flexibility characterized by an elongation to break ≥30%, and/or c) a modulus consistent with elastomeric character (as appreciated in the art) between 0.1 and 100 MPa. In other embodiments, the silicone encapsulant is opaque ((e.g. when utilized in/as a remote phosphor or a die attach).

Polyorganosiloxane (Composition):

The polyorganosiloxane first introduced above as utilized in the encapsulant is not particularly limited and may be any in the art. In one embodiment, the polyorganosiloxane is curable. In another embodiment, the polyorganosiloxane is cured, e.g. prior to, concurrently with, or after, addition of the additive. In still other embodiments, the polyorganosiloxane is not curable and may be, for example, a silicone fluid such as PDMS.

In various embodiments, the polyorganosiloxane has a viscosity of from greater than zero to less than 500,000, 450,000, 400,000, 350,000, 300,000, 250,000, 200,000, 150,000, 100,000, 50,000, 25,000, 20,000, 15,000, 10,000, or 5,000, centistokes measured at 25° C. In other embodiments, the polyorganosiloxane has a viscosity of from 5,000 to 50,000, from 10,000 to 45,000, from 15,000 to 40,000, from 20,000 to 35,000, from 25,000 to 30,000, centistokes measured at 25° C. Alternatively, the polyorganosiloxane may have a viscosity of any value or range of values between any of the aforementioned values.

Curable Polyorganosiloxane (Composition):

As described above, the polyorganosiloxane (composition) may be curable. Examples of curable polyorganosiloxanes (and compositions) include, but are not limited to, hydrosilylation-curable polyorganosiloxanes, condensation-curable polyorganosiloxanes, radiation-curable polyorganosiloxanes, and peroxide-curable polyorganosiloxanes.

In one embodiment, the polyorganosiloxane (composition) is hydrosilylation curable or condensation curable. In another embodiment, the polyorganosiloxane (composition) is hydrosilylation curable. In still another embodiment, the polyorganosiloxane (composition) is condensation curable. The polyorganosiloxane (composition) can be cured by exposure to ambient temperature, elevated temperature, moisture, or radiation, depending on the type of polyorganosiloxane(s) present.

A hydrosilylation-curable polyorganosiloxane composition typically includes a polyorganosiloxane that has an average of at least two silicon-bonded alkenyl groups or silicon-bonded hydrogen atoms per molecule. This composition also typically includes an organosilicon compound in an amount sufficient to cure the polyorganosiloxane composition, wherein the organosilicon compound typically has an average of at least two silicon-bonded hydrogen atoms or silicon-bonded alkenyl groups per molecule capable of reacting with the silicon-bonded alkenyl groups or silicon-bonded hydrogen atoms of the polyorganosiloxane. The composition may also include a catalytic amount of a hydrosilylation catalyst. Typically, this type of polyorganosiloxane composition can be cured by exposure to a temperature of from room temperature (~23±2° C.) to 250° C., alternatively from room temperature to 150° C., alternatively from room temperature to 115° C., at atmospheric pressure. The polyorganosiloxane composition is generally heated for a length of time sufficient to cure (cross-link) the polyorganosiloxane.

A condensation-curable polyorganosiloxane composition typically includes a polyorganosiloxane having an average of at least two silicon-bonded hydrogen atoms, hydroxy groups, or hydrolysable groups per molecule and, optionally, a cross-linking agent having silicon-bonded hydrolysable groups and/or a condensation catalyst. Typically, this type of composition cures depending on the nature of the silicon-bonded groups of the polyorganosiloxane. For example, when a polyorganosiloxane includes silicon-bonded hydroxy groups, the composition can be cured (i.e., cross-linked) by heating. The composition can typically be cured by heating at a temperature of from 50 to 250° C., for a period of from 1 to 50 h. When the condensation-curable polyorganosiloxane includes a condensation catalyst, the composition can typically be cured at a lower temperature, e.g., from room temperature (~23±2° C.) to 150° C.

Alternatively, condensation-curable polyorganosiloxane compositions that include a polyorganosiloxane having silicon-bonded hydrogen atoms can be cured by exposing the composition to moisture or oxygen at a temperature of from 100 to 450° C. for a period of from 0.1 to 20 h. When the condensation-curable polyorganosiloxane includes a condensation catalyst, the composition can typically be cured at a lower temperature, e.g., from room temperature (~23±2° C.) to 400° C. Further, condensation-curable polyorganosiloxane composition that include a polyorganosiloxane having silicon-bonded hydrolysable groups can be cured by exposing the composition to moisture at a temperature of from room temperature (~23±2° C.) to 250° C., alternatively from 100 to 200° C., for a period of from 1 to 100 h. For example, the polyorganosiloxane can typically be cured by exposing it to a relative humidity of 30% at a temperature of from about room temperature (~23±2° C.) to 150° C., for a period of from 0.5 to 72 h. Cure can be accelerated by application of heat, exposure to high humidity, and/or addition of a condensation catalyst to the composition.

A peroxide-curable polyorganosiloxane composition typically includes a polyorganosiloxane having silicon-bonded unsaturated aliphatic hydrocarbon groups and an organic peroxide. Such a composition can typically be cured by exposure to a temperature of from room temperature (~23±2° C.) to 180° C., for a period of from 0.05 to 1 h.

A radiation-curable polyorganosiloxane composition typically includes a polyorganosiloxane having an average of at least two silicon-bonded radiation-sensitive groups per molecule and, optionally, a cationic or free-radical photoinitiator depending on the nature of the radiation-sensitive groups in the polyorganosiloxane. Such a composition can typically be cured by exposing the composition to an electron beam and/or ultraviolet radiation. Typically, the accelerating voltage is from about 0.1 to 100 keV, the vacuum is from about 10 to 10-3 Pa, the electron current is from about 0.0001 to 1 ampere, and the power varies from about 0.1 watt to 1 kilowatt. The dose is typically from about 100 microcoulomb/cm$^2$ to 100 coulomb/cm$^2$, alternatively from about 1 to 10 coulombs/cm$^2$. Depending on the voltage, the time of exposure is typically from about 10 seconds to 1 hour. Also, if such a composition includes a cationic or free radical photoinitiator, the composition can typically be cured by exposing it to radiation having a wavelength of from 150 to 800 nm, alternatively from 200 to 400 nm, at a dosage sufficient to cure. The light source is typically a medium pressure mercury-arc lamp. The dose of radiation is typically from 30 to 1,000 mJ/cm$^2$, alternatively from 50 to 500 mJ/cm$^2$. Moreover, the polyorganosiloxane can be externally heated during or after exposure to radiation to enhance the rate and/or extent of cure.

Cured Polyorganosiloxane (Composition):

The aforementioned cured polyorganosiloxane (composition) may be alternatively described as the cured product of any one or more of the aforementioned curable compositions. Typically, the additive is added to a cured composition prior to curing. However, it is contemplated that the additive may be added to a cured composition after that composition has been cured. For example, the additive may be physically mixed or blended with the composition after the composition has been cured.

Non-Curable Polyorganosiloxane (Composition):

The aforementioned non-curable polyorganosiloxane (composition) may be alternatively described as a silicone fluid that is non-reactive. A typical silicone fluid is PDMS. In various embodiments, the silicone fluid has a viscosity at 25° C. of from about 0.001 to about 50 Pa·s, typically from about 0.02 to about 10 Pa·s, and more typically from about 0.05 to about 5 Pa·s. The silicone fluid can be linear, branched, cyclic, or a mixture thereof. Mixtures of the aforementioned fluids may also be used. Many of the linear, branched, and cyclic silicone fluids have melting points below about 25° C. Such materials are also commonly described as silicone liquids, silicone fluids, or silicone oils. A detailed description of non-limiting silicone fluids can be found in many references, including "Chemistry and Technology of Silicones" by W. Knoll, Academic Press, 1968, which, in one embodiment, is incorporated herein by reference relative to the silicone fluids.

Non-limiting examples of linear silicone fluids suitable for use herein include trimethylsiloxy-terminated dimethylsiloxane fluids sold by Dow Corning Corporation under the trade name "Dow Corning® 200 Fluids". These silicone fluids are manufactured to yield essentially linear oligomers and/or polymers typically having a viscosity of from 0.001 to about 50 Pa·s at 25° C. Such fluids are primarily linear but can include cyclic and/or branched structures. In one embodiment, the silicone fluid is a trimethylsiloxy-terminated polydimethylsiloxane having a viscosity of about 0.1 Pa·s at 25° C.

Additional non-limiting examples of suitable cyclic silicone fluids include the cyclic polydimethylsiloxanes sold by Dow Corning Corporation under the trade names "Dow Corning® 244, 245, 344, and 345 Fluids", depending on the relative proportions of octamethylcyclotetrasiloxane and decamethylcyclopentasiloxane. Mixtures of the straight-chain and cyclic dimethyl may also be utilized. Even additional non-limiting examples of suitable silicone fluids are $Me_3SiO[(OSiMe_3)_2SiO]SiMe_3$ and $Me_3SiO[(OSiMe_3)MeSiO]SiMe_3$.

Additional Components:

The encapsulant and/or any of the aforementioned polyorganosiloxane (compositions) may include one or more additional components such as catalysts, fillers, other reactants, light activated compounds such as phosphors or quantum dots, etc.

Device:

This disclosure also provides a device. The device may be used for various applications. In various embodiments, the device is or includes a power modules based on Si substrates or wide band gap semiconductor substrates that operate at ever-increasing temperatures. For example, the power module can be used for power inversion. In other embodiments, the device includes a dielectric gel, potant, or overmold. For example, the device may include an electronic component and an encapsulant, e.g. as a gel, including the additive, disposed on the electronic component as protection, e.g. as a dielectric, physical, or gas/liquid barrier. In various embodiments, the additive is utilized in a composition, such as a silicone encapsulant, that is used to protect power modules and other electronic components from the environment when used in high operating temperature devices at temperatures >150° C., >180° C., >200° C., >225° C., and up to 250° C., 300° C., 350° C., or 400° C.

In certain embodiments, the device is used for solid-state lighting (SSL) applications. For example, one or more of the devices may be used for general lighting applications, such as for lighting residential, commercial, and/or industrial spaces. Such lighting may be direct lighting, indirect lighting, or a combination thereof. The device can be used separately or in an array. The device may be used for other applications as well, such as for automotive applications, display applications, backlighting applications, etc. While the device is especially useful for general lighting applications, the device is not limited to any particular application. The device may be of various constructs. For example, the device may be configured as a light bulb, a luminaire, a light engine, or a lamp. The device may be configured into any type of construct. For example, the device may include an optoelectronic component and the encapsulant, e.g. as a gel, disposed on the optoelectronic component as protection, e.g. as a dielectric, physical, or gas/liquid barrier. In still other embodiments, the device may be or include a remote phosphor binder, a secondary optic and/or light guide, a white reflector, a phosphor conversion layer binder, or a die attach adhesive film. In other embodiments, the device may be or include a light guide panel, light guide sheet, light guide film, etc. or a wave guide.

The device may be or includes the optoelectronic component and the encapsulant, including the additive, disposed on the optoelectronic component. The optoelectronic component is not particularly limited and may be further defined as an optoelectronic semiconductor. Alternatively, the optoelectronic component may be further defined as a component that sources and/or detects and controls light such as visible light, gamma rays, x-rays, ultraviolet rays, and infrared rays. In various embodiments, the optoelectronic component is a photovoltaic (solar) cell or (light emitting) diodes.

Optoelectronic semiconductors typically operate as electrical-to-optical or optical-to-electrical transducers. Typical, but non-limiting optoelectronic semiconductors include photodiodes including solar cells, phototransistors, photomultipliers, integrated optical circuit (IOC) elements, photoresistors, photoconductive camera tubes, charge-coupled imaging devices, injection laser diodes, quantum cascade lasers, light-emitting diodes, photoemissive camera tubes, and the like. In one embodiment, the optoelectronic semiconductor is further defined as a solar cell. In another embodiment, the optoelectronic semiconductor is further defined as a light emitting diode.

The optoelectronic semiconductor is not particularly limited and may be any known in the art. Typically, the optoelectronic semiconductor has an electrical conductivity of from about $10^3$ S/cm to about $10^{-8}$ S/cm. In one embodiment, the optoelectronic semiconductor includes silicon. In other embodiments, the optoelectronic semiconductor includes arsenic, selenium, tellurium, germanium, gallium arsenide, silicon carbide, and/or elements from Groups IV, III-V, II-VI, I-VII, IV-VI, V-VI, and II-V, and may be of p- or n-type. It is contemplated that the optoelectronic semiconductor (12) may be disposed on a substrate, such as glass, using chemical vapor deposition (CVD).

The optoelectronic semiconductor has a first side and a second side. Typically the first side is opposite the second side. However, the first and second sides may be adjacent each other. In various embodiments, one or more of electrical leads are attached to one or both of the first and second sides to connect a series of optoelectronic semiconductors together. The electrical leads may be of any size and shape and typically are rectangular-shaped. In one embodiment, the electrical leads have dimensions of approximately 0.005 to 0.080 inches in length and/or width. In other embodiments, the electrical leads have a thickness of from 0.005 to 0.015, from 0.005 to 0.010, or from 0.007 to 0.010, inches. The electrical leads may be of any type known in the art and may be disposed on any portion of the optoelectronic semiconductor.

Typically, one electrical lead acts as an anode while another electrical lead acts as a cathode. In various embodiments, the optoelectronic semiconductor includes one or more electrical leads disposed thereon, e.g. first, second, third, and fourth electrical leads. These electrical leads may be the same or may be different from each other (i.e., made from the same material or from different materials) and may include metals, conducting polymers, and combinations thereof. In one embodiment, the one or more electrical leads include tin-silver solder coated copper. In another embodiment, the one or more electrical leads include tin-lead solder coated copper. The optoelectronic semiconductor itself is not limited in size or shape and may be any size or shape known in the art.

Light Emitting Diode:

The light emitting diode may also be referred to in the art as a semiconductor diode, chip or die. In certain embodiments, the device can further comprise at least one supplemental light emitting diode spaced from the light emitting diode. As such, the device may include a plurality of light emitting diodes. If multiple light emitting diodes are utilized to form the device, the light emitting diodes may be the same as or different from each other. For example, the light emitting diodes may be of the same or different sizes, shapes, and/or colors. The light emitting diode can emit various wavelengths (or spectrums) of light. As specific examples, one light emitting diode may emit blue light, one light emitting diode may red light, one light emitting diode may emit green light, one light emitting diode may emit near-ultraviolet (near-UV) light, and/or one light emitting diode may emit UV light.

In certain embodiments, the light emitting diode is of the type that generally emits blue light. In related embodiments, the device includes at least one supplemental light emitting diode in addition to the blue light emitting diode which is of the type that generally emits red, green, or near-UV, light. As such, the device can include various combinations of one or more light emitting diodes which emit various combinations of colors, such as: i) blue light; ii) blue and red light; iii) red, green, and blue, light; iv) near-UV light; v) UV light; etc. In one embodiment, one of the light emitting diodes emits blue light and the other light emitting diode emits another color, such as red light.

The light emitting diode can be formed from various materials. Typically, the light emitting diode is formed from a semiconductor material. Various types of semiconductor materials may be utilized to form the light emitting diode. In certain embodiments, the semiconductor material is one capable of emitting blue light, such as zinc selenide (ZnSe) or indium gallium nitride (InGaN). Other types of materials may be used to emit other colors. For example, the light emitting diode may comprise various combinations of gallium, nitride, indium, arsenic, aluminum, phosphide, zinc, selenide, silicon, and/or carbon. In one embodiment, the light emitting diode comprises gallium nitride. In another embodiment, the light emitting diode comprises indium gallium nitride.

In certain embodiments, the light emitting diode comprises a semiconductor and an epitaxial layer disposed on the semiconductor. The semiconductor and epitaxial layer can be formed from various materials. In certain embodiments, the semiconductor comprises sapphire, silicon (Si), silicon carbide (SiC), or combinations thereof. In related embodiments, the epitaxial layer comprises gallium, nitride, indium, aluminum, phosphide, zinc, selenide, gallium nitride, indium gallium nitride, aluminum gallium nitride, aluminum indium gallium nitride, zinc selenide, or combinations thereof.

The light emitting diode generally emits a first radiation spectrum having an average wavelength ($\lambda_1$) in the infrared to ultraviolet light range. By "average wavelength", it is generally meant that the average wavelength is the intensity weighted average wavelength resulting from the overall spectrum of radiation being emitted, such that the apparent color of the emitted spectrum would correspond to the color of radiation at the average wavelength only. The average wavelength may be calculated from the formula:

$$\lambda_a = \frac{\int_0^\infty I(\lambda')\lambda' d\lambda'}{\int_0^\infty I(\lambda') d\lambda'}$$

where I is the intensity or power, $\lambda$ is the wavelength, and $\lambda_a$ is the average wavelength. Alternatively, the average wavelength weighted to the luminous intensity may be calculated by the formula:

$$\lambda_a = \frac{\int_0^\infty P(\lambda')I(\lambda')\lambda' d\lambda'}{\int_0^\infty P(\lambda')I(\lambda') d\lambda'}$$

where P is photopic response function which correlates optical power to the apparent brightness, as described in Robinson, S. J. and Schmidt, J. T., Fluorescent Penetrant Sensitivity and Removability—What the Eye Can See, a Fluorometer Can Measure, Materials Evaluation, Vol. 42, No. 8, July 1984, pp. 1029-1034.

Alternatively, the average wavelength may also be referred to as a peak and/or median wavelength of the spectrum emitted. For example, if the emitted spectrum were to have a Gaussian distribution, or bell curve shape, the average wavelength would be located at the center or peak. This does not mean that the average wavelength cannot be offset from center, as the peak of intensity is oftentimes located in the leftmost or rightmost area of the actual emitted spectrum as many spectrums tend to be asymmetrical.

In certain embodiments, the light emitting diode emits an $\lambda_1$ of from about 100 to about 550, about 250 to about 550, about 350 to about 525, about 400 to about 500, about 425 to about 500, about 450 to about 500, about 460 to about 490, about 465 to about 475, about 465 to about 470, or about 465, nm. Such average wavelengths (and their surrounding spectrum) generally correspond to "blue/green", "bluish", "blue", or "true blue", light.

If utilized, the supplemental light emitting diode generally emits a supplemental radiation spectrum having an average wavelength ($\lambda_S$) in the infrared to ultraviolet light range. In certain embodiments, the supplemental light emitting diode emits a $\lambda_S$ corresponding to: "red" light having an $\lambda_S$ of from about 575 nm to about 850 nm; "green" light having an $\lambda_S$ of from about 475 nm to about 585 nm; "blue" light having an $\lambda_S$ of from about 400 nm to about 500 nm; or "near-UV" light having an $\lambda_S$ of from about 0 nm to about 450 nm. As described above, more than one (supplemental) light emitting diode may be utilized to form the device.

The device may also include a luminescent layer. The luminescent layer may be disposed directly on the light emitting diode or spaced apart from the light emitting diode. Similarly, the luminescent layer may be disposed directly on the encapsulant or spaced apart from the encapsulant.

In embodiments wherein the luminescent layer is in direct contact with the light emitting diode, i.e., there is not an intervening layer disposed between the luminescent layer and the light emitting diode, such arrangements may be referred to in the art as "on-chip" constructs. In embodiments wherein the luminescent layer is spaced from the light emitting diode, such arrangements may be referred to in the art as "remote" or "remote on-chip" constructs. Constructs having a plurality of such arrangements, i.e., two or more light emitting diodes having their own respective luminescent layers, may be referred to in the art as integral on-chip, on-chip, or remote on-chip "packages", relative to the arrangements described above. Such packages may have different combinations of various light emitting diodes and/or luminescent layers, which may be the same as or different from each other, as alluded to above. The present invention is not limited to any specific construct, as constructs in the art can vary greatly in design and/or complexity.

The luminescent layer may cover only a portion of the light emitting diode, such as a top surface of the light emitting diode. In other embodiments, the luminescent layer substantially covers all of the light emitting diode. For example, the luminescent layer may cover the top surface and sides of the light emitting diode. If present, the supplemental light emitting diode may include or be free of the luminescent layer. Such embodiments can be useful to present different colors.

The luminescent layer may be of various sizes, shapes, and configurations. Thickness of the luminescent layer may be uniform or may vary. In certain embodiments, the luminescent layer has a substantially dome-shaped cross section defined by the luminescent layer and the light emitting diode. In other embodiments, the luminescent layer has a substantially rectangular-shaped cross section defined by the luminescent layer and the light emitting diode. The luminescent layer may be of other shapes as well. For example, the luminescent layer can have a substantially frustoconical-shaped cross section defined by the luminescent layer and the light emitting diode.

The luminescent layer typically includes a host material. The host material can be of various chemistries. The host material may also be described as a binder or a carrier. In various embodiments, the host material includes a polycarbonate, an epoxy (e.g. a polyepoxide), a polyurethane, a silicone, an acrylate (e.g. a methacrylate), or combinations thereof.

In certain embodiments, the host material includes a silicone or polyorganosiloxane, such as any one or more of those described above. Various types of silicones can be utilized to form the luminescent layer. Typically, the silicone is optically transparent so as to not interfere with light emitted by the light emitting diode or the luminescent layer. Such properties provide excellent aesthetics and light output of the device. The host material may be generally non-scattering which provides similar benefits and excellent efficiency of the device.

In certain embodiments, host material includes a polymer, which can be further described as a homopolymer or a copolymer. The polymer can alternatively be described as a thermoset polymer or a thermoplastic polymer. Typically, as used herein and below, the term "thermoplastic polymer" describes a polymer that has the physical property of converting to a fluid (flowable) state when heated and of becoming rigid (non-flowable) when cooled. Also, the term "thermoset polymer" may describe a cured (i.e., cross-linked) polymer that does not convert to a fluid state on heating. Non-limiting examples of thermoplastic polymers include, but are not limited to thermoplastic organic polymers such as polyolefins, polysulfones, polyacrylates and polyetherimides, and combinations thereof.

As used herein and below, the term "thermoset polymer" typically describes a polymer having the property of becoming permanently rigid (non-flowable) when cured (i.e., cross-linked). Non-limiting examples of thermoset polymers include, but are not limited to, epoxy resins, cured amino resins, cured polyurethanes, cured polyimides, cured phenolic resins, cured cyanate ester resins, cured bismaleimide resins, cured polyesters, and cured acrylic resins. The polymer is typically an organic polymer, as the term is generally appreciated by those of skill in the art.

In one embodiment, the organic polymer is not particularly limited and may be any organic polymer known in the art. In an alternative embodiment, the polymer is chosen from polycarbonates, polyalkylenes, nylons, polystyrenes, polyesters, polyvinylchlorides, polyalkylacrylates, polyalkylalkacylates, and combinations thereof. In still another embodiment, the polymer is chosen from polyurethanes, epoxy polymers, polycarbonates, polyalkylenes, nylons, polystyrenes, polyesters, polyvinylchlorides, polyalkylalkacrylates, and combinations thereof. In a further embodiment, the polymer is chosen from polyolefins such as polyethylene, polypropylene, polystyrene, and polyethyleneterephthalate, fluorocarbon polymers such as polytetrafluoroethylene and polyvinylfluoride, polyamides such as nylons, polyimides, polyesters such as poly(methyl methacrylate), polyethers, polycarbonates, polysulfones, and polyether sulfones, and combinations thereof.

The luminescent layer may further include a luminescent compound in the host material. The luminescent compound typically does not substantially contribute to a haze value of the luminescent layer while in the luminescent layer. The haze value of the luminescent layer can be used as a measure of the degree of scattering imparted by the luminescent compound. Haze values can be determined by utilizing the test method as described in ASTM D1003 or a modification thereof.

In certain embodiments, the luminescent layer is non-scattering as alluded to above. In these embodiments, "non-scattering" is generally indicated by a haze value of no greater than about 30%, no greater than about 20%, no greater than about 15%, no greater than about 10%, no greater than about 8%, no greater than about 6%, no greater than about 5%, no greater than about 4%, no greater than about 2%, or no greater than about 0.5%, according to ASTM D1003-07, modified. The test method is typically modified such that a test specimen (i.e., a sample of the luminescent layer formed from the host material and luminescent compound) has an average thickness of about 3.2 mm rather than the thickness required by the standard test method. Little to no haze in the luminescent layer provides for excellent aesthetics, light output, and efficiency of the device.

Substrate/Superstrate:

The device may also include a substrate and/or a superstrate. Typically, the substrate provides protection to a rear surface of the device while a superstrate typically provides protection to a front surface of the device. The substrate and the superstrate may be the same or may be different and each may independently include any suitable material known in the art. The substrate and/or superstrate may be soft and flexible or may be rigid and stiff. Alternatively, the substrate and/or superstrate may include rigid and stiff segments while simultaneously including soft and flexible segments. The substrate and/or superstrate may be transparent to light, may be opaque, or may not transmit light (i.e., may be impervious to light). Typically, the superstrate transmits light. In one embodiment, the substrate and/or superstrate includes glass. In another embodiment, the substrate and/or superstrate includes metal foils, polyimides, ethylene-vinyl acetate copolymers, and/or organic fluoropolymers including, but not limited to, ethylene tetrafluoroethylene (ETFE), Tedlar®, polyester/Tedlar®, Tedlar®/polyester/Tedlar®, polyethylene terephthalate (PET) alone or coated with silicon and oxygenated materials ($SiO_x$), and combinations thereof. In one embodiment, the substrate is further defined as a PET/$SiO_x$-PET/A1 substrate, wherein x has a value of from 1 to 4.

The substrate and/or superstrate may be load bearing or non-load bearing and may be included in any portion of the device. Typically, the substrate is load bearing. The substrate may be a "bottom layer" of the device that is typically positioned behind the optoelectronic semiconductor and serves as mechanical support. Alternatively, the device may include a second or additional substrate and/or superstrate. The substrate may be the bottom layer of the device while a second substrate may be the top layer and function as the superstrate. Typically, the second substrate (e.g. a second substrate functioning as a superstrate is transparent to the solar spectrum (e.g. visible light) and is positioned on top of the substrate. The second substrate may be positioned in front of a light source. The second substrate may be used to protect the device from environmental conditions such as rain, show, and heat. Most typically, the second substrate functions as a superstrate and is a rigid glass panel that is transparent to sunlight and is used to protect the front surface of the device.

The substrate and/or superstrate typically have a thickness of from 50 to 500, of from 100 to 225, or of from 175 to 225, micrometers. The substrate and/or superstrate may have a length and width of 125 mm each or a length and width of 156 mm each. of course, the invention is not limited to these thicknesses or ranges thereof and the thickness of the substrate and/or superstrate may be any value or range of values, both whole and fractional, within those ranges and values described above or different therefrom. It is also contemplated that the thickness, length, and/or width of the substrate and/or superstrate may vary from the values and/or range of values above by ±5%, ±10%, ±15%, ±20%, ±25%, ±30%, etc.

Referring back, the device also includes the encapsulant that is disposed on the optoelectronic component. The terminology "disposed on" includes the encapsulant disposed on and in direct contact with the optoelectronic device. This terminology also includes the encapsulant spaced apart from the optoelectronic device yet still disposed thereon. The encapsulant may be disposed on the optoelectronic device such that only one side of the optoelectronic device is covered. Alternatively, the encapsulant may partially or entirely encapsulate the optoelectronic device or any other component described herein. In various embodiments, the encapsulant is a sheet, gel, film, paste, or liquid. Most typically, the encapsulant is a sheet or a film. It is contemplated that, in various embodiments, the additive and the silicone encapsulant may be used to form one part of a device or the entire device itself.

Additional Components:

In certain embodiments, the device further comprises a light transmissive cover disposed over the luminescent layer and/or encapsulant, e.g. opposite the light emitting diode. If utilized, the light transmissive cover is typically spaced from the luminescent layer and/or encapsulant. The light transmissive cover may be formed from various materials and may be formed from a material that is the same as or different from the material of the host material of the luminescent layer and/or encapsulant. In certain embodiments, the light transmissive cover is formed from a glass, an epoxy, or a polycarbonate. The light transmissive cover is useful for protecting the luminescent layer, the encapsulant, and/or the light emitting diode.

In various embodiments, the device further comprises at least one reflector, e.g. disposed adjacent the light emitting diode. The reflector is typically spaced from at least a portion of the luminescent layer and/or encapsulant. The reflector can be of various shapes, and typically has a dish, parabolic, or frustoconical shape. The light emitting diode is typically disposed in the middle of the reflector. However, the light emitting diode may also be offset from center. The reflector can be formed from various materials, such as a metal. Various types of metals can be used to form the reflector and other materials may be used as well provided they provide a degree of reflection. The reflector may be useful for directing light emitted by the light emitting diode and, optionally, the luminescent layer and/or encapsulant, outwardly away from the device.

In further embodiments, the device can comprise any number of other additional components generally associated with conventional light emitting devices. For example, the device can include one or more wire bonds, a submount, and/or a heat sink. As further examples, the device can comprise a circuit board and/or a lens. If utilized, the circuit board can be programmed to include lighting controls such as dimming, light sensing and pre-set timing. Such controls are especially useful for packages.

Method of Making the Device:

This disclosure also provides a method of making the device. The method includes the step of disposing the silicone encapsulant on the optoelectronic component. In one embodiment, the step of disposing is further defined as disposing the silicone encapsulant on and in direct contact with the optoelectronic component. In another embodiment, the step of disposing is further defined as disposing the silicone encapsulant on and apart from the optoelectronic component.

The encapsulant and/or any one or more compositions or components described above may be deposited by any means known in the art including using a brush/trowel, spraying, pouring, dipping, utilizing a dispensing nozzle, roll coating, transfer printing, screen printing, curtain coating, or any method known in the art. It is contemplated that the step of depositing may be alternatively described as dispensing, disposing, applying, or coating. In one embodiment, the method may include first dispensing, e.g. through one or more spray nozzles, followed by manual troweling and optionally a combination of dispensing a mass followed by automated troweling. For example, this may be possible when utilizing long pot life compositions.

The method may also include the step of laminating any one or more of the aforementioned components or layers. The step of laminating is not particularly limited and may include any one or more laminating techniques known in the art. For example, the step of laminating may be described as contacting and/or compressing any one or more of the above with another. The step of compressing may include applying a mechanical weight, press, or roller (e.g. a pinch roller). The step of compressing may be further defined as applying a force on the interior (e.g. at the center) of the device or any one or more layers of components. This force may be moved towards the perimeter or edges of the device. For example, this force may be applied at the center and then moved outwards to assist in the evacuation of air from the device.

The step of laminating or, for example compressing, may also include the step of applying a vacuum to one or more of the aforementioned components. Alternatively, the step of applying a vacuum may be performed independent of the step of laminating or compressing or may not be utilized at all. Still further, the step of laminating may include the step of applying heat to one or more of the aforementioned components. Alternatively, the step of applying heat may be independent from the step of laminating or compressing or not be utilized at all.

EXAMPLES

A first series of examples that include the encapsulant and the additive are formed. These Examples include a PDMS test matrix as the encapsulant that is formed from a mixture of Dimethylvinylsiloxy-terminated Dimethyl Siloxane and Trimethylsiloxy-terminated Dimethyl, Methylhydrogen siloxane that are reacted at an SiH: Vinyl ratio of 1.0 in the presence of 5 ppm of Pt complexed with dimethylvinylsiloxy terminated PDMS. These examples include varying amounts (5-2000 ppm) of cerium in one or more additives. A comparative example is also formed and is identical to the aforementioned but does not include any additive.

A second series of examples includes a phenyl test matrix as the encapsulant formed from a mixture of Dimethylvinylsiloxy-terminated methylphenylsiloxane, Tetramethyltetravinylcyclotetrasiloxane, Phenylsilsesquioxane, dimethylhydrogen-terminated, and Dimethylhydrogen-terminated diphenylsiloxane that are reacted at an SiH:Vinyl ratio of 1.0 in the presence of 2.5 ppm of Pt complexed to dimethylvinylsiloxy-terminated methylphenylsiloxane. These examples include varying amounts (5-2000 ppm) of cerium in one or more additives. A second comparative sample is also formed and is identical to the immediately aforementioned second series of examples but does not include any additive.

To form the examples, the components (and optionally the additives) are mixed and cast and press cured as a 1.5 mm thick slab heating to 150° C. for 15 minutes such that the reactants react and cure to form slabs. The slabs are then removed from the mold and placed in a 120° C. oven for 4 hours to complete the cure.

Samples of the slabs are evaluated to determine elongation and compression modulus, i.e., to evaluate brittleness. These samples are prepared by using a standard die cut method to a sample form of a standard tensile bar or 8 mm (diam) disc.

To determine compression modulus, compression modulus discs are aged in foil pans and tested via the method set forth below. Aging is accomplished at 225° C. as described above. Compression modulus testing is performed using a TA.XT2i Texture Analyzer (Stable Micro Systems) equipped with a 1-kg capacity, 0.1-g force resolution, load cell and aligned 10 mm diameter flat cylindrical test fixtures to compress the samples. The samples are 8 mm discs die cut from 1.5 mm thick hot pressed test slabs that were tested following aging by placing the aged disc adhered to the foil pans on the center of the lower stationary probe.

A compression strain from 0-50% is applied to the samples at a test speed of 0.1 mm/s. The strain is determined from the probe travel distance, d, and the sample thickness, h, as shown in equation 1: $\epsilon(\%) = d/h \times 100$ (1)

Compressive moduli, Ec, of the elastomer discs are calculated from the slope of the compressive stress (compressive force divided by sample cross-sectional area) vs applied strain experimental data over the strain range of 15-35% where the samples exhibit uniform behavior.

In the Examples and throughout this disclosure, the terminology "$Ce^{Me}$" describes tetrakis((1,1,1,3,5,5,5-heptamethyltrisiloxan-3-yl)oxy)cerium. Similarly, the terminology "$Ce^{mePh}$" describes tetrakis((1,3,5-trimethyl-1,1,5,5-tetraphenyltrisiloxan-3-yl)oxy)cerium. Further, the terminology "$Ce(III)^{Me}$" describes tris((1,1,1,3,5,5,5-heptamethyltrisiloxan-3-yl)oxy)cerium.

PDMS Test Matrix:

More specifically, elongation and compression modulus testing results of the examples that utilize the PDMS test matrix are set forth in the Tables below:

| | Elongation Testing (% Elongation to Break) Ageing Time 225° C. in air (Days) | | | | | | | | | | |
|---|---|---|---|---|---|---|---|---|---|---|---|
| | Ageing Time (Days) | | | | | | | | | | |
| | 0 | 0.33 | 1 | 2 | 3 | 5 | 7 | 10 | 14 | 20 | 30 |
| Comparative Example 1 | 387 | N/A | 362 | 133 | N/A | 61 | N/A | 34 | N/A | 15 | 7 |
| Example 1 ($Ce^{Me}$) | 419 | N/A | 171 | 139 | N/A | 164 | N/A | 125 | N/A | 99 | 70 |
| Example 2 ($Ce(III)^{Me}$) | 263 | 263 | 272 | N/A | 179 | N/A | 122 | 110 | 93 | 64 | 63 |

Comparative Example 1 includes no additive.

Example 1 includes 200 ppm of cerium delivered in/as tetrakis((1,1,1,3,5,5,5-heptamethyltrisiloxan-3-yl)oxy)cerium as the additive.

Example 2 includes 200 ppm of cerium delivered in/as tris((1,1,1,3,5,5,5-heptamethyltrisiloxan-3-yl)oxy)cerium as the additive.

The data set forth above demonstrates that adding a cerium silyloxy stabilizer to the dimethylsilicone matrix is very effective at resisting hardening on exposure to high temperatures (as measured by % elongation to break) which is important for stable performance in devices. 50-1000 ppm of the additive in the matrix is suitable to obtain a significant benefit.

The compression modulus testing results of the PDMS matrix samples is set forth in the Tables below:

| | Compression Modulus Testing (MPa) Ageing Time 225° C. in air (Days) | | | | | | | | |
|---|---|---|---|---|---|---|---|---|---|
| | Ageing Time (Days) | | | | | | | | |
| | 0 | 0.33 | 1 | 3 | 7 | 10 | 14 | 20 | 30 |
| Comparative Example 1 | 2.42 | 2.34 | 1.11 | 10.35 | 16.94 | N/A | 24.19 | N/A | N/A |
| Example 3 5 ppm Cerium Delivered In/As CeMe | 2.32 | 2.17 | 2.12 | 1.895 | 3.37 | 10.52 | N/A | 11.54 | 12.66 |

Compression Modulus Testing (MPa)
Ageing Time 225° C. in air (Days)

| | Ageing Time (Days) | | | | | | | | |
|---|---|---|---|---|---|---|---|---|---|
| | 0 | 0.33 | 1 | 3 | 7 | 10 | 14 | 20 | 30 |
| Example 4 50 ppm Cerium Delivered In/As CeMe | 2.49 | 2.20 | 2.05 | 1.85 | 2.93 | 3.25 | 4.03 | 3.29 | 5.26 |
| Example 1 200 ppm Cerium Delivered In/As CeMe | 2.5 | 1.89 | 1.74 | 1.34 | 1.69 | 1.52 | 2.42 | 1.87 | 3.05 |
| Example 5 750 ppm Cerium Delivered In/As CeMe | 2.13 | 1.49 | 1.29 | 0.77 | 1.08 | 1.37 | 1.61 | 1.26 | 1.65 |
| Comparative Example 1 | 2.42 | 2.35 | 1.11 | 10.35 | 16.94 | N/A | 24.19 | N/A | N/A |
| Example 6 5 ppm Cerium Delivered In/As Ce(III)Me | 2.64 | 2.44 | 2.36 | 2.34 | 3.12 | 11.47 | 13.99 | N/A | 14.63 |
| Example 7 50 ppm Cerium Delivered In/As Ce(III)Me | 2.66 | 2.53 | 2.35 | 2.32 | 2.80 | 3.20 | 3.81 | 3.08 | 1.08 |
| Example 2 200 ppm Cerium Delivered In/As Ce(III)Me | 2.56 | 2.53 | 1.97 | 1.28 | 1.91 | 2.20 | 2.62 | 1.98 | 1.92 |
| Example 8 750 ppm Cerium Delivered In/As Ce(III)Me | 1.78 | 1.53 | 1.33 | 1.12 | 1.46 | 1.8 | 1.8 | 1.54 | 1.57 |

Comparative Example 1 includes no additive.

Example 6 includes 5 ppm of cerium delivered in/as tetrakis((1,1,1,3,5,5,5-heptamethyltrisiloxan-3-yl)oxy)cerium as the additive.

Example 7 includes 50 ppm of cerium delivered in/as tetrakis((1,1,1,3,5,5,5-heptamethyltrisiloxan-3-yl)oxy)cerium as the additive.

Example 8 includes 750 ppm of cerium delivered in/as tetrakis((1,1,1,3,5,5,5-heptamethyltrisiloxan-3-yl)oxy)cerium as the additive.

The data set forth above demonstrates that adding a cerium silyloxy stabilizer to the dimethylsilicone matrix is very effective at resisting hardening on exposure to high temperatures (as measured by modulus) which is important for stable performance in devices. 50-1000 ppm cerium delivered in/as the additive in the matrix is suitable to obtain a significant benefit.

Phenyl Test Matrix:

The elongation and compression testing results of the phenyl matrix samples are set forth in the Tables below:

Elongation Testing (% Elongation to Break)
Ageing Time 225° C. in air (Days)

| | Ageing Time (Days) | | | | | | | | |
|---|---|---|---|---|---|---|---|---|---|
| | 0 | 0.33 | 1 | 3 | 7 | 10 | 14 | 20 | 30 |
| Comparative Example 2 | 68 | 59 | 33 | 8 | 3 | 2 | 3 | 4 | 4 |
| Example 3 ($Ce^{MePh}$) | 54 | 58 | 65 | 69 | 37 | 24 | 26 | 7 | 4 |

Comparative Example 2 includes no additive.

Example 3 includes 200 ppm of cerium delivered in/as tetrakis((1,3,5-trimethyl-1,1,5,5-tetraphenyltrisiloxan-3-yl)oxy)cerium as the additive.

The data set forth above demonstrates that adding a cerium silyloxy stabilizer to the methylphenylsilicone matrix is very effective at resisting hardening on exposure to high temperatures (as measured by % elongation to break) which is important for stable performance in devices. 50-1000 ppm of cerium delivered in/as the additive in the matrix is suitable to obtain a significant benefit.

The compression modulus testing results of the phenyl matrix samples is set forth in the Tables below:

| | Compression Modulus Testing (MPa) Ageing Time 225° C. in air (Days) | | | | | | | | |
|---|---|---|---|---|---|---|---|---|---|
| | Ageing Time (Days) | | | | | | | | |
| | 0 | 0.33 | 1 | 3 | 7 | 10 | 14 | 20 | 30 |
| Comparative Example 2 | 6.16 | 3.61 | 3.82 | 6.01 | 17.59 | 28.04 | 40.21 | 36.90 | 34.54 |
| Example 9 5 ppm Cerium Delivered In/As CeMePh | 6.00 | 3.98 | 2.03 | 6.75 | 11.04 | 36.9 | 42.52 | 42.33 | 34.45 |
| Example 10 50 ppm Cerium Delivered In/As CeMePh | 4.9 | 3.66 | 3.48 | 4.74 | 29.17 | 40.89 | 42.01 | 40.85 | 34.6 |
| Example 3 | 3.73 | 4.49 | 4.33 | 3.49 | 4.24 | 4.90 | 10.11 | 9.38 | 10.83 |
| Example 11 750 ppm Cerium Delivered In/As CeMePh | 1.7 | 4.39 | 4.36 | 2.93 | 5.07 | 4.65 | 4.86 | 4.71 | 5.40 |

Comparative Example 2 includes no additive.

Example 9 includes 5 ppm of cerium delivered in/as tetrakis((1,3,5-trimethyl-1,1,5,5-tetraphenyltrisiloxan-3-yl)oxy)cerium as the additive.

Example 10 includes 50 ppm of cerium delivered in/as tetrakis((1,3,5-trimethyl-1,1,5,5-tetraphenyltrisiloxan-3-yl)oxy)cerium as the additive.

Example 3 is as described above.

Example 11 includes 750 ppm of cerium delivered in/as tetrakis((1,3,5-trimethyl-1,1,5,5-tetraphenyltrisiloxan-3-yl)oxy)cerium as the additive.

The data set forth above demonstrates that adding a cerium silyloxy stabilizer to the methylphenylsilicone matrix is very effective at resisting hardening on exposure to high temperatures (as measured by modulus) which is important for stable performance in devices. 50-1000 ppm of cerium delivered in/as the additive in the matrix is suitable to obtain a significant benefit.

Samples of the phenyl matrix are also tested to evaluate yellowing over time. Yellowing may be reported as CIE b*, which is a measure of the yellow vs blue color of a reflecting surface. The more positive value for b* the more yellow the material appears relative to blue. Negative b* values in increasing magnitude signify more blue color. Materials with b*=0 do not exhibit blue nor yellow color. Hence, the yellowing of a material under an exposure can be monitored by measuring b*. Samples for the b* measurement are cast directly into Al foil pans to a depth of 2.5 mm and determined using CIE 1976L*a*bD$_{65}$(illumination angle)/10(observation angle) color test method. Aging is accomplished at 225° C. as described above. The sample are removed from the pan and placed on a calibrated white background before color measurements.

| | Yellowness Testing Ageing Time 225° C. in air (Days) | | | | | | | | |
|---|---|---|---|---|---|---|---|---|---|
| Example | Day 0 | Day 0.33 | Day 1 | Day 3 | Day 7 | Day 10 | Day 14 | Day 20 | Day 30 |
| Comparative Example 2 | 1.32 | 10.56 | 11.49 | 22.64 | 29.70 | 32.86 | 37.00 | 48.30 | 49.54 |
| Example 9 5 ppm Cerium Delivered In/As CeMePh CeMePh | 1.51 | 9.49 | 14.52 | 28.42 | 30.88 | 33.11 | 42.60 | 44.34 | 41.28 |
| Example 10 50 ppm Cerium Delivered In/As CeMePh CeMePh | 2.05 | 5.84 | 10.28 | 14.21 | 16.67 | 23.82 | 29.56 | 34.46 | 40.28 |
| Example 3 | 4.49 | 6.47 | 6.91 | 7.45 | 8.22 | 9.82 | 10.77 | 10.96 | 12.27 |
| Example 11 | | | | | | | | | |

-continued

| | Yellowness Testing Ageing Time 225° C. in air (Days) | | | | | | | | |
|---|---|---|---|---|---|---|---|---|---|
| Example | Day 0 | Day 0.33 | Day 1 | Day 3 | Day 7 | Day 10 | Day 14 | Day 20 | Day 30 |
| 750 ppm Cerium Delivered In/As CeMePh CeMePh | 12.41 | 13.90 | 16.56 | 18.12 | 24.33 | 25.58 | 29.75 | 33.51 | 36.13 |
| Example 12 2000 ppm Cerium Delivered In/As CeMePh CeMePh | 31.32 | 32.42 | 38.80 | 41.31 | 57.01 | 57.65 | 64.82 | 55.53 | 57.68 |

Example 12 includes 2000 ppm of cerium delivered in/as tetrakis((1,3,5-trimethyl-1,1,5,5-tetraphenyl-3-yl)oxy)cerium as the additive.

The data set forth above demonstrates that adding a cerium silyloxy stabilizer to the methylphenylsilicone matrix is very effective at resisting discoloration upon exposure to high temperatures (as measured by CIE b*) which is important for stable performance of the silicone encapsulant in devices. 50-1000 ppm of the cerium delivered in/as additive in the matrix is suitable to obtain a significant benefit.

Inductively Coupled Plasma-Optical Emission Spectrometer (ICP-OES) Analysis:

ICP-OES analysis is also performed. More specifically, additives $Ce^{Me}$, $Ce(III)^{Me}$, and $Ce^{MePh}$ are evaluated to determine theoretical amounts of Ce and actual amounts of Ce. Typically, all data is adjusted for instrument drift and matrix differences with the 1 ppm Sc internal standard. This adjustment is generally +/-0-5%. More specifically, ~0.05 grams of sample is weighed into a platinum dish. The samples are charred using $H_2SO_4$, taken to dryness then placed in a furnace to remove any residual carbon. The samples are then digested using $H_2SO_4$, $HNO_3$, and HF. The samples are taken to near dryness, then, brought to a final volume of 20 ml using ~5% $HNO_3$. A 2nd 15× dilution into 5% $HNO_3$ is performed prior to analysis. 1 ppm of Sc is added as an internal standard. The samples are then analyzed via Inductively Coupled Plasma-Optical Emission Spectrometer (ICP-OES).

In the samples with high levels of Ce, there is a significant interference in the Sc wavelength that skews the internal standard result and subsequently the amount that is corrected the samples. This is rare. The high Ce samples are reprocessed without internal standard correction and that data is set forth below. In addition, the variance in the actual content of Ce is expected and can fall within a range that is determined by numerous experimental and environmental factors, e.g. synthetic pathway and moisture exposure.

| Compound | Theoretical % Ce | Actual % Ce |
|---|---|---|
| Structure I: $Ce^{Me}$ Tetrakis((1,1,1,3,5,5,5-heptamethyltrisiloxan-3-yl)oxy)cerium | 12.85 | 12.9 |

-continued

| Compound | Theoretical % Ce | Actual % Ce |
|---|---|---|
| Structure III: $Ce(III)^{Me}$ Tris((1,1,1,3,5,5,5-heptamethyltrisiloxan-3-yl)oxy)cerium | 16.43 | 21.0 |
| Structure II: $Ce^{MePh}$ Tetrakis((1,3,5-trimethyl-1,1,5,5-tetraphenyltrisiloxan-3-yl)oxy)cerium | 6.73 | 4.2 |

The aforementioned data show that analysis of the Ce content of the aforementioned compounds enables refined targeting of final metal content in an article or composition. The molecular complexity of Ce and the variety of possible synthetic methods leading to the additives allow for variance of the final metal content.

In various non-limiting embodiments, this disclosure includes one or more compounds, method steps, devices, or analytical steps, or any other description, as set forth in the simultaneously filed U.S. Provisional Patent Application No. 61/873,081, which is expressly incorporated herein in its entirety relative to these non-limiting embodiments.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

What is claimed is:

1. An additive for a silicone encapsulant, said additive having the structure:

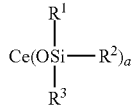

wherein subscript a is 3 or 4,
wherein $R^1$ and $R^2$ are each —O—Si($R^4$)($R^5$)($R^6$) and each of $R^4$, $R^5$, and $R^6$ is independently chosen from $C_1$-$C_{10}$ hydrocarbyl groups, $C_1$-$C_{10}$ alkenyl groups, $C_2$-$C_2$ $C_{10}$ alkenyl groups, and $C_6$-$C_{10}$ aryl groups, and wherein $R^3$ is independently chosen from $C_1$-$C_{10}$ hydrocarbyl groups, $C_1$ -$C_{10}$ alkyl groups, $C_2$-$C_{10}$ alkenyl groups, and $C_6$-$C_{10}$ aryl groups.

2. The additive of claim 1 wherein at least 20 mol percent of a total of the groups $R^3$-$R^6$ are methyl groups.

3. The additive of claim 1 wherein at least 20 mol percent of a total of the groups $R^3$-$R^6$ are phenyl groups.

4. The additive of claim 1 wherein each $R^3$, $R^4$, and $R^6$ is a methyl group.

5. The additive of claim 1 wherein each $R^3$, $R^4$, and $R^6$ is a phenyl group.

6. The additive of claim 1 that is further defined as having the structure:

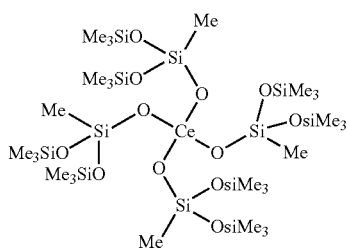

wherein Me is methyl.

7. The additive of claim 1 that is further defined as having the structure:

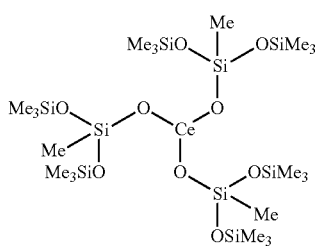

wherein Me is methyl.

8. The additive of claim 1 that is further defined as having the structure:

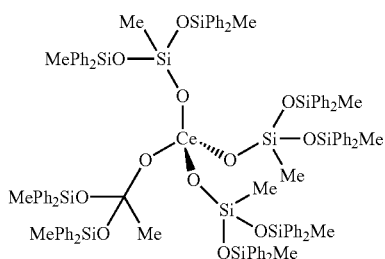

wherein Me is methyl and Ph is phenyl.

9. The additive of any preceding claim that is further defined as:

a reaction product of a reaction of a cerium alkoxide and a hydroxyl functional organosiloxane; or a reaction product of a reaction of cerium ammonium nitrate and a hydroxyl functional organosiloxane; or a reaction product of a reaction of cerium metal and a hydroxyl functional organosiloxane; or an exchange reaction product of a reaction of a trifunctional silyloxy cerium (III) or (IV) compound and a hydroxyl functional organosiloxane.

10. The additive of claim 9 wherein the hydroxyl functional organosiloxane has the formula $M^1 D^{R,OH} M^2$, wherein R is chosen from $C_1$-$C_{10}$ hydrocarbyl groups, $C_1$ -$C_{10}$ alkyl groups, $C_2$-$C_{10}$ alkenyl groups, and $C_6$ -$C_{10}$ aryl groups.

11. The additive of claim 1 having a density of from 0.95 to 1.2 g/cm$^3$.

12. The additive of claim 1 that is free of an alkaline metal salt and/or alkaline earth metal salt.

13. The additive of claim 1 that comprises 3 to 25 weight percent of cerium based on a total weight of said additive.

14. A cerium silyloxide cluster comprising 2 to 10 units of the additive of claim 1.

15. A silicone encapsulant comprising said additive of claims 1 and a silicone.

16. A silicone encapsulant comprising:
A. an additive having the structure:

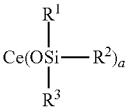

wherein subscript a is 3 or 4,
wherein $R^1$ and $R^2$ are each —O—Si($R^4$)($R^5$)($R^6$) and each of $R^4$, $R^5$, and $R^6$ is independently chosen from $C_1$-$C_{10}$ hydrocarbyl groups, $C_1$ -$C_{10}$ alkyl groups, $C_2$ -$C_{10}$ alkenyl groups, and $C_6$ -$C_{10}$ aryl groups, and wherein $R^3$ is independently chosen from $C_1$ -$C_{10}$ hydrocarbyl groups, $C_1$-$C_{10}$ alkyl groups, $C_2$-$C_{10}$ alkenyl groups, and $C_6$ -$C_{10}$ aryl groups; and
B. a polyorganosiloxane.

17. A device comprising an optoelectronic component and said encapsulant of claim 16.

18. A method of making an additive having the structure:

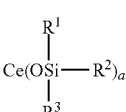

wherein subscript a is 3 or 4,
wherein $R^1$ and $R^2$ are each —O—Si($R^4$)($R^5$)($R^6$) and each of $R^4$, $R^5$, and $R^6$ is independently chosen from $C_1$-$C_{10}$ hydrocarbyl groups, $C_1$ -$C_{10}$ alkyl groups, $C_2$-$C_{10}$ alkenyl groups, and $C_6$-$C_{10}$ aryl groups, and wherein $R^3$ is independently chosen from $C_1$-$C_{10}$ hydrocarbyl groups, $C_1$-$C_{10}$ alkyl groups, $C_2$ -$C_{10}$ alkenyl groups, and $C_6$-$C_{10}$ aryl groups,
wherein the method comprises the step of reacting cerium metal or a cerium (III) or (IV) compound with a hydroxyl functional organosiloxane.

* * * * *